United States Patent
Weingarten

(10) Patent No.: US 7,622,604 B2
(45) Date of Patent: *Nov. 24, 2009

(54) PROCESS OF PREPARING ESTERS AND ETHERS OF PROBUCOL AND DERIVATIVES THEREOF

(75) Inventor: M. David Weingarten, Cumming, GA (US)

(73) Assignee: Salutria Pharmaceuticals LLC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/854,939

(22) Filed: Sep. 13, 2007

(65) Prior Publication Data

US 2008/0009642 A1    Jan. 10, 2008

Related U.S. Application Data

(63) Continuation of application No. 10/757,664, filed on Jan. 13, 2004, now Pat. No. 7,273,948.

(60) Provisional application No. 60/439,665, filed on Jan. 13, 2003.

(51) Int. Cl.
 *C07C 69/035* (2006.01)
(52) U.S. Cl. .................................................... 560/142
(58) Field of Classification Search .................. None
 See application file for complete search history.

(56) References Cited

U.S. PATENT DOCUMENTS

| | | | |
|---|---|---|---|
| 3,576,883 A | 4/1971 | Neuworth |
| 3,952,064 A | 4/1976 | Whalley |
| 4,752,616 A | 6/1988 | Hall et al. |
| 5,155,250 A | 10/1992 | Parker et al. |
| 5,206,247 A | 4/1993 | Regnier et al. |
| 5,262,439 A | 11/1993 | Parthasarathy |
| 5,294,724 A | 3/1994 | Jendralla et al. |
| 5,380,747 A | 1/1995 | Medford et al. |
| 5,608,095 A | 3/1997 | Parker et al. |
| 5,627,205 A | 5/1997 | Regnier et al. |
| 5,783,596 A | 7/1998 | Medford et al. |
| 5,792,787 A | 8/1998 | Medford et al. |
| 6,121,319 A | 9/2000 | Somers |
| 6,147,250 A | 11/2000 | Somers |
| 6,323,359 B1 | 11/2001 | Jass |
| 6,548,699 B1 | 4/2003 | Somers |
| 6,602,914 B2 | 8/2003 | Meng |
| 6,617,352 B2 | 9/2003 | Somers |
| 6,670,398 B2 | 12/2003 | Edwards et al. |
| 6,806,381 B2 | 10/2004 | Chidambaram et al. |
| 6,828,447 B2 | 12/2004 | Meng |
| 7,087,645 B2 | 8/2006 | Galss et al. |
| 7,189,870 B2 | 3/2007 | Somers |
| 7,273,948 B2 * | 9/2007 | Weingarten et al. ......... 560/173 |
| 7,294,737 B2 | 11/2007 | Weingarten |
| 2006/0025481 A1 | 2/2006 | Strange |

FOREIGN PATENT DOCUMENTS

| | | |
|---|---|---|
| EP | 0 418 648 A1 | 3/1991 |
| EP | 0 763 527 A1 | 3/1997 |
| FR | 2.130.975 | 11/1972 |
| FR | 2.133.024 | 11/1972 |
| FR | 2.134.810 | 12/1972 |
| FR | 2.140.769 | 1/1973 |
| FR | 2.140.771 | 1/1973 |
| FR | 2.168.137 | 8/1973 |
| WO | WO 98/51289 A2 | 11/1998 |
| WO | WO 98/51662 A2 | 11/1998 |
| WO | WO 01/70757 A2 | 9/2001 |

OTHER PUBLICATIONS

Aldrich, Aldrich Chemical Catalog, 2002, Milwaukee, WI, pp. 187, 1104, 1454 and 1597.
De Meglio, P., et al. New derivatives of clofibrate and probucol. Preliminary studies on hypolipemic activity, Farmaco, Ed. Sci., 1985, 40(11), 833-844. [In Italian; abstract provided in English: *Chem Abstr*. AN 1986:28675, DN 104:28675; & partial transl. in English.
Fruebis, J., et al., "A comparison of the antiatherogenic effects of probucol and of a structural analogue of probucol in low-density lipoprotein receptor-deficient rabbits," *J. Clinical Investigation*, 94:392-398 (Jul. 1994).
Mamedov, Ch.I., "Synthesis of sulfur-containing derivatives of 2,6-di-tert-butylphenols," *Mater. Nauchn. Konf. Akad. Nauk. Az. SSR*, 1:1,27-131 (1980), in Russian. English language abstract provided as *Chem. Abstr*. 94:302790c (1981), p. 528.
Meng, C.Q., et al., "Novel phenolic antioxidants as multifunctional inhibitors of inducible VCAM-1 expression for use in atherosclerosis," *Bioorganic & Medicinal Chemistry Letters*, 12:2545-2548 (2002).
Neuworth, M.B., et al. "Synthesis and hypocholesterolemic activity of alkylidenedithio bisphenols," *J. Med. Chem.*, 13(4):722-725 (1970).
Tardif, J.-C., et al., "Clinical results with AGI-1067: A novel antioxidant vascular protectant," *Amer. J. Cardiol.*, 91(suppl.):41A-49A (Feb. 2003).

* cited by examiner

*Primary Examiner*—Paul A Zucker
(74) *Attorney, Agent, or Firm*—King & Spalding

(57) ABSTRACT

A probucol or a probucol derivative can be efficiently converted to a monoester or monoether of probucol by reacting the free hydroxyl-containing probucol or a derivative thereof (by which is meant a probucol compound with at least one substituent that is different from that on the parent probucol molecule but which maintains the two free hydroxyl groups) with a Grignard reagent or a lithium reagent that produces a magnesium bromide or lithium salt of probucol or the probucol derivative. The probucol compound anion is then reacted with an ester or ether forming compound.

17 Claims, No Drawings

PROCESS OF PREPARING ESTERS AND ETHERS OF PROBUCOL AND DERIVATIVES THEREOF

CROSS REFERENCE TO RELATED APPLICATIONS

This application is a continuation of U.S. application Ser. No. 10/757,664, filed Jan. 13, 2004, now U.S. Pat. No. 7,273,948, which claims priority to U.S. Provisional Application Ser. No. 60/439,665, filed Jan. 13, 2003.

FIELD OF THE INVENTION

The present invention is a process for the manufacture of esters and ethers of probucol and derivatives thereof that are suitable for the treatment of inflammatory and cardiovascular diseases.

BACKGROUND OF THE INVENTION

U.S. Pat. No. 5,262,439 to Parthasarathy, which is assigned to AtheroGenics, Inc. discloses analogs of probucol with increased water solubility in which one or both of the hydroxyl groups are replaced with ester groups that increase the water solubility of the compound. The '439 patent reports that carboxylic acid derivatives of probucol can be prepared by treating probucol with an excess of dicarboxylic acid anhydride and catalytic amounts of 4-dimethyl-aminopyridine at a temperature sufficient to ensure that the dicarboxylic acid anhydride is liquid. Under these conditions, no anhydrous solvent is necessary, as the anhydride itself acts as a solvent.

WO 01/70757 filed by AtheroGenics, Inc. describes the use of certain compounds of the following formula, and pharmaceutically acceptable salts thereof along with method of use and methods of manufacturing:

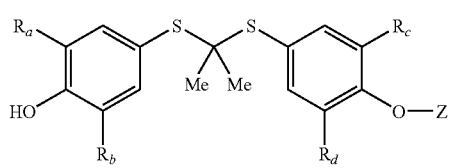

(I)

wherein
a) $R_a$, $R_b$, $R_c$, and $R_d$ are independently any group that does not adversely affect the desired properties of the molecule, including hydrogen, alkyl, substituted alkyl, aryl, substituted aryl, heteroaryl, substituted heteroaryl, alkaryl, substituted alkaryl, aralkyl, or substituted aralkyl; and
b) Z is (i) a substituted or unsubstituted carbohydrate, (ii) a substituted or unsubstituted alditol, (iii) $C_{1-10}$alkyl or substituted $C_{1-10}$alkyl, terminated by sulfonic acid, (iv) $C_{1-10}$alkyl or substituted $C_{1-10}$alkyl, terminated by phosphonic acid, (v) substituted or unsubstituted $C_{1-10}$alkyl-O—C(O)—$C_{1-10}$alkyl, (vi) straight chained polyhydroxylated $C_{3-10}$ alkyl; (vii) —$(CR_2)_{1-6}$—COOH, wherein R is independently hydrogen, halo, amino, or hydroxy, and wherein at least one of the R substituents is not hydrogen; or (viii) —$(CR_2)_{1-6}$—X, wherein X is aryl, heteroaryl, or heterocycle, and R is independently hydrogen, halo, amino, or hydroxy.

U.S. Pat. No. 6,147,250, assigned to AtheroGenics, Inc., provides compounds, compositions, method for inhibiting the expression of VCAM-1, and methods of preparing said compounds and compositions. The patent reports that a monoester can be prepared by treating a quantity of probucol in a 0.1 M solution of tetrahydrofuran with 2 equivalents of sodium hydride and stirred at room temperature for 30 minutes. To the reaction mixture is added 3 equivalents of an acid chloride or acid anhydride and the reaction stirred at room temperature for 16 hours. The reaction is quenched with 1 N HCl and diluted with ethyl acetate. The aqueous layer is removed and the ethyl acetate layer is washed with water and then with an aqueous saturated sodium chloride solution. The ethyl acetate solution is dried over magnesium sulfate, gravity or vacuum filtered, and then concentrated. The product is purified by silica gel chromatography yielding 14% of the desired compound.

U.S. Pat. No. 6,323,359 discloses and claims methods of manufacturing a group of compounds found in the '250 patent. The '359 patent discloses the use of alkali metal hydroxide, alkali metal alkoxide, alkali ammonium alkoxide, alkyl ammonium hydroxide to form alkali metal salts of probucol compounds and then reacting the salts with dicarboxylic acid anhydride.

French Patent Publication No. 2.168.137 describes the production of diesters of probucol by reacting probucol with a halide or anhydride of an organic acid in an inert solvent with heat and in the presence of a base such as an alkaline hydroxide or carbonate, a tertiary amine or a tertiary nitrogenous heterocycle. The O-metallic derivative of probucol can also be used as the reaction intermediate.

What is still needed is a method of manufacturing a group of compounds described in U.S. Pat. Nos. 6,141,250; 6,323,359; 5,262,439; and WO 01/70757 that is efficient and gives good yields.

It is another object of the invention to provide a process for the preparation of monoesters and monoethers of probucol or a probucol derivative that optimizes the amount of final product.

It is yet another object of the present invention to provide a process for the preparation of monoesters and monoethers of probucol or a probucol derivative that minimizes the amount of reagent used.

SUMMARY OF THE INVENTION

A process for the preparation of esters and ethers of probucol or a probucol derivative is provided that optimizes the amount of monoester in the final product mixture and minimizes the amount of reagents.

It has been discovered that probucol or a derivative thereof can be efficiently converted to esters of probucol by reacting a free hydroxyl-containing probucol or a derivative thereof (by which is meant a probucol compound with at least one substituent that is different from that on the parent probucol molecule but which maintains the two free hydroxyl groups) with a Grignard reagent or a lithium reagent that produces a magnesium salt or lithium salt of probucol or the probucol derivative, respectively. The probucol compound salt with strong oxide anion is then reacted with an ester forming compound such as a saturated or unsaturated acyl halide, saturated or unsaturated carboxylic acid anhydride, a saturated or unsaturated activated carboxylic acid ester or other ester-forming reagent. The probucol compound salt can alternatively be reacted with an ether forming compound to generate a probucol ether or probucol ether derivative.

In a broad description, the invention consists of processes to manufacturing a compound of Formula I and salts thereof

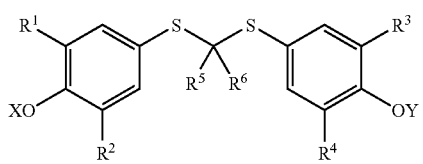

wherein $R^1$, $R^2$, $R^3$, and $R^4$ are independently selected from the group consisting of hydrogen and alkyl, said alkyl optionally substituted by hydroxy, alkyl, alkenyl, acyl, nitro, amino, halo, carboxy and cyano;

$R^5$ and $R^6$ are the same or different and independently selected from the group consisting of alkyl, alkenyl, and aryl all of which can be optionally substituted by hydroxy, alkyl, alkenyl, acyl, nitro, amino, halo, carboxy and cyano;

$R^5$ and $R^6$ can come together to form a carbocyclic ring;

X is selected from the group consisting of hydrogen, an optionally substituted unsaturated acyl, and an optionally substituted saturated acyl, said optionally substituted unsaturated acyl and optionally substituted saturated acyl optionally containing a polar or charged functionality;

Y is selected from the group consisting of an optionally substituted unsaturated acyl and an optionally substituted saturated acyl, said optionally substituted unsaturated acyl and optionally substituted saturated acyl optionally containing a polar or charged functionality;

comprising:

reacting a compound of Formula II

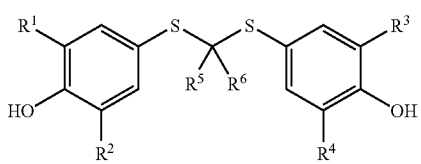

wherein $R^1$, $R^2$, $R^3$, $R^4$, $R^5$ and $R^6$ are as previously defined, with a Grignard Reagent to form a magnesium salt or a reagent selected from the group consisting of alkyl lithium, alkenyl lithium, alkynyl lithium, aryl lithium, aralkyl lithium, and a heteroaryl lithium, all which can be optionally substituted, to form a lithium salt;

reacting said magnesium salt or lithium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, amino, halo, protected carboxy and cyano;

separating and isolating said compound of Formula I or salts thereof; or

X is selected from the group consisting of hydrogen, an optionally substituted unsaturated alkyl, and an optionally substituted saturated alkyl, said optionally substituted unsaturated alkyl and optionally substituted saturated alkyl optionally containing a polar or charged functionality;

Y is selected from the group consisting of an optionally substituted unsaturated alkyl, and an optionally substituted saturated alkyl, said optionally substituted unsaturated alkyl and optionally substituted saturated alkyl optionally containing a polar or charged functionality;

comprising:

reacting a compound of Formula II wherein $R^1$, $R^2$, $R^3$, $R^4$, $R^5$ and $R^6$ are as previously defined, with a Grignard Reagent to form a magnesium salt or a reagent selected from the group consisting of alkyl lithium, alkenyl lithium, alkynyl lithium, aryl lithium, aralkyl lithium, and a heteroaryl lithium, all which can be optionally substituted, to form a lithium salt;

reacting said magnesium salt or lithium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, amino, halo, protected carboxy, epoxide and cyano;

separating and isolating said compound of Formula I or salts thereof.

DETAILED DESCRIPTION OF THE INVENTION

A process for the preparation of an ester of probucol or a probucol derivative is provided that optimizes the amount of final product and minimizes the amount of reagents used.

Probucol or a probucol derivative thereof can be converted to a monoester of probucol or probucol derivative by reacting the probucol or probucol derivative thereof with a Grignard reagent or a lithium reagent that produces a magnesium salt or lithium salt of probucol or the probucol derivative, respectively. The resulting probucol salt is then reacted with an ester forming compound such as a saturated or unsaturated acyl halide, saturated or unsaturated carboxylic acid anhydride, a saturated or unsaturated activated carboxylic acid ester or other ester-forming reagent, all of which may be optionally substituted.

Product ratios of about 64% monoester (wherein 66% monoester constitutes the expected theoretical yield), about 13% diester and about 23% unreacted probucol or probucol derivative can be achieved by the optimized selection of reaction conditions.

In another embodiment, the invention provides a process for the preparation of an ether of probucol or a probucol derivative that optimizes the amount of the final product and minimizes the amount of reagents used.

Probucol or a probucol derivative can be converted to a monoether of probucol or probucol derivative by reacting the probucol or probucol derivative thereof with a Grignard reagent or a lithium reagent that produces a magnesium salt or lithium salt of probucol or the probucol derivative, respectively. The resulting probucol salt is then reacted with an ether forming compound such as an alkyl halide, alkyl tosylate, alkyl mesylate, other alkyl group with an appropriate leaving group or other ether-forming reagent, all of which may be optionally substituted.

Any solvent can be used that achieves the desired results. Examples of solvents include any organic solvent that is inert under the reaction conditions, aprotic solvents, ethers (such as THF or ethyl ether), liquid amides (such as DMF), hydrocarbons (including aromatic hydrocarbons such as toluene) and mixtures thereof. The word solvent as used herein includes mixtures of solvents. Solubilizing reagents as used herein include but are not limited to tetramethylurea; 1,3-dimethyl-3,4,5,6-tetrahydro-2(1H)-pyrimidinone and hexamethylphosphoramide. Generally, alcohols or other reagents that could react with a Grignard reagent or lithium reagent should be avoided.

Typically the reaction is carried out in an inert atmosphere such as under a nitrogen or argon blanket.

In the first step of the reaction, probucol or a probucol derivative is mixed with a Grignard reagent or lithium reagent in the presence of a solvent, co-solvent or solubilizing reagent or mixtures thereof to form a probucol salt.

In the second step, the probucol salt is reacted with the ester or ether forming agent. The probucol salt of the first step can be isolated and used in the second step at a later time or both the first and second steps can take place in a single reaction vessel by simply introducing the ester or ether forming reagent either neat or in a suitable solvent to the probucol salt mixture. Alternatively, the probucol salt mixture can be added to a reaction vessel that contains the ester or ether forming agent either neat or in an appropriate solvent.

The first and second steps can be carried out at the same or different temperatures, or both or either can be reacted under gradient temperatures. Both steps generally are carried out at any temperature(s) that achieve the desired results.

The reactions are maintained at low temperature, including any temperature to about or just above the freezing point of the solvent. In other embodiments, the temperature of either or both of the reactions range from below 0° C. to room temperature or higher, including up to the boiling point of the solvent. The selection of temperature can depend on the preference of the operator, the available equipment, the freezing and boiling points of the solvent or solvents used, the reactivity of the reagents, and the control of side reactions.

Alternatively, the natural exotherm of either or both of the reactions are used to warm the reaction and to avoid the need for external application of heat. Excessive or undesired exotherms may be controlled with external cooling.

In another aspect of the invention, a Grignard reagent or a lithium reagent is added to a mixture containing probucol or a probucol derivative and an ester or ether forming agent in a solvent, co-solvent, or solubilizing agent or mixtures thereof.

In a particularly broad form, the invention encompasses methods of manufacturing compounds of Formula I or salts thereof

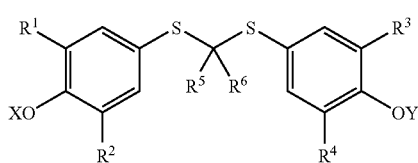

wherein $R^1$, $R^2$, $R^3$, and $R^4$ are independently selected from the group consisting of hydrogen and alkyl, said alkyl optionally substituted by hydroxy, alkyl, alkenyl, acyl, nitro, amino, halo, carboxy and cyano;

$R^5$ and $R^6$ are the same or different and independently selected from the group consisting of alkyl, alkenyl, and aryl all of which can be optionally substituted by hydroxy, alkyl, alkenyl, acyl, nitro, amino, halo, carboxy and cyano;

$R^5$ and $R^6$ can come together to form a carbocyclic ring;

X is selected from the group consisting of hydrogen, an optionally substituted unsaturated acyl, and an optionally substituted saturated acyl, said optionally substituted unsaturated acyl and optionally substituted saturated acyl optionally containing a polar or charged functionality;

Y is selected from the group consisting of an optionally substituted unsaturated acyl and an optionally substituted saturated acyl, said optionally substituted unsaturated acyl and optionally substituted saturated acyl optionally containing a polar or charged functionality;

comprising:

reacting a compound of Formula II

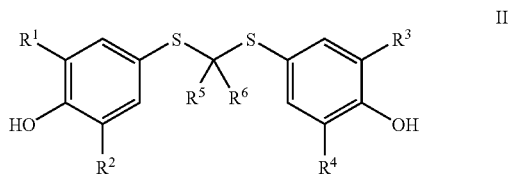

wherein $R^1$, $R^2$, $R^3$, $R^4$, $R^5$ and $R^6$ are as previously defined, with a Grignard Reagent to form a magnesium salt or a reagent selected from the group consisting of alkyl lithium, alkenyl lithium, alkynyl lithium, aryl lithium, aralkyl lithium, and a heteroaryl lithium, all which can be optionally substituted, to form a lithium salt;

reacting said magnesium salt or lithium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, amino, halo, protected carboxy and cyano;

separating and isolating said compound of Formula I or salts thereof, or

X is selected from the group consisting of hydrogen, an optionally substituted unsaturated alkyl, and an optionally substituted saturated alkyl, said optionally substituted unsaturated alkyl and optionally substituted saturated alkyl optionally containing a polar or charged functionality;

Y is selected from the group consisting of an optionally substituted unsaturated alkyl, and an optionally substituted saturated alkyl, said optionally substituted unsaturated alkyl and optionally substituted saturated alkyl optionally containing a polar or charged functionality;

comprising:

reacting a compound of Formula II wherein $R^1$, $R^2$, $R^3$, $R^4$, $R^5$ and $R^6$ are as previously defined, with a Grignard Reagent to form a magnesium salt or a reagent selected from the group consisting of alkyl lithium, alkenyl lithium, alkynyl lithium, aryl lithium, aralkyl lithium, and a heteroaryl lithium, all which can be optionally substituted, to form a lithium salt;

reacting said magnesium salt or lithium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, amino, halo, protected carboxy, epoxide and cyano;

separating and isolating said compound of Formula I or salts thereof.

In a 1st narrowed embodiment, the invention encompasses processes of manufacturing compounds of Formula I or salts thereof

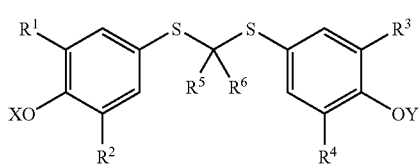

I wherein $R^1$, $R^2$, $R^3$, and $R^4$ are the same or different and independently selected from the group consisting of hydrogen and an alkyl having from 1 to 6 carbon atoms;

$R^5$ and $R^6$ are the same or different and independently selected from the group consisting of an alkyl having from 1 to 8 carbon atoms, an alkenyl having from 2 to 8 carbon atoms, and aryl;

$R^5$ and $R^6$ can come together to form a carbocyclic ring containing from 3 to 8 carbon atoms;

X is selected from the group consisting of hydrogen, an optionally substituted unsaturated acyl having from 1 to 18 carbon atoms, and an optionally substituted saturated acyl having from 1 to 18 carbon atoms, said optionally substituted unsaturated acyl and optionally substituted saturated acyl optionally containing a polar or charged functionality;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula II

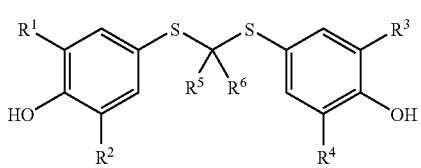

II wherein $R^1$, $R^2$, $R^3$, $R^4$, $R^5$ and $R^6$ are as previously defined, with a Grignard Reagent to form a magnesium salt or a reagent selected from the group consisting of an alkyl lithium, alkenyl lithium, alkynyl lithium, aryl lithium, aralkyl lithium, and a heteroaryl lithium, all which can be optionally substituted to form a lithium salt; reacting said magnesium salt or lithium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, amino, halo, protected carboxy and cyano;

separating and isolating said compound of Formula I or salts thereof, or

X is selected from the group consisting of hydrogen, an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula II wherein $R^1$, $R^2$, $R^3$, $R^4$, $R^5$ and $R^6$ are as previously defined, with a Grignard Reagent to form a magnesium salt or a reagent selected from the group consisting of an alkyl lithium, alkenyl lithium, alkynyl lithium, aryl lithium, aralkyl lithium, and a heteroaryl lithium, all which can be optionally substituted to form a lithium salt;

reacting said magnesium salt or lithium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano; separating and isolating said compound of Formula I or salts thereof.

In a 2nd embodiment, the invention is represented by the process to manufacture a compound of Formula III or salts thereof

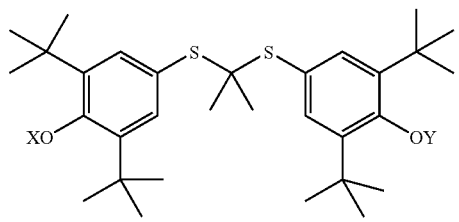

III wherein:

X is selected from the group consisting of hydrogen, an optionally substituted unsaturated acyl having from 1 to 18 carbon atoms, and an optionally substituted saturated acyl having from 1 to 18 carbon atoms, said optionally substituted unsaturated acyl and optionally substituted saturated acyl optionally containing a polar or charged functionality;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV

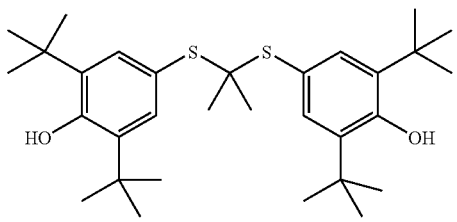

IV with a Grignard Reagent to form a magnesium salt or a reagent selected from the group consisting of an alkyl lithium, alkenyl lithium, alkynyl lithium, aryl lithium, aralkyl lithium, and a heteroaryl lithium, all which can be optionally substituted to form a lithium salt;

reacting said magnesium salt or lithium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, amino, halo, protected carboxy and cyano;

separating and isolating said compound of Formula III or salts thereof.

In a 3rd embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent to form a magnesium salt or a reagent selected from the group consisting of an alkyl lithium, alkenyl lithium, alkynyl lithium, aryl lithium, aralkyl lithium, and a heteroaryl lithium, all which can be optionally substituted to form a lithium salt;

reacting said magnesium salt or lithium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, halo, protected carboxy and cyano;

separating and isolating said compound of Formula III or salts thereof.

In a 4$^{th}$ embodiment, the invention is represented by the process to manufacture a compound of Formula III or salts thereof wherein:

X is selected from the group consisting of hydrogen, an optionally substituted unsaturated acyl having from 1 to 18 carbon atoms, and an optionally substituted saturated acyl having from 1 to 18 carbon atoms, said optionally substituted unsaturated acyl and optionally substituted saturated acyl optionally containing a polar or charged functionality;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent to form a magnesium salt; reacting said magnesium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 5$^{th}$ embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent to form a magnesium salt; reacting said magnesium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 6$^{th}$ embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of alkylmagnesium halide, alkenylmagnesium halide, alkynylmagnesium halide, arylmagnesium halide, arylalkylmagnesium halide, alkylmagnesium alkyl, arylmagnesium aryl, arylalkynylmagnesium halide, arylalkenylmagnesium halide, and heteroarylmagnesium halide, all of which may optionally be substituted by one or more selected from the group consisting of protected hydroxy, alkyl, alkenyl, protected acyl, nitro, protected amino, halo and protected carboxy, to form a magnesium salt; reacting said magnesium salt with a compound selected from the group consisting of a saturated or unsaturated carboxylic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 7th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a solution of a compound of Formula IV

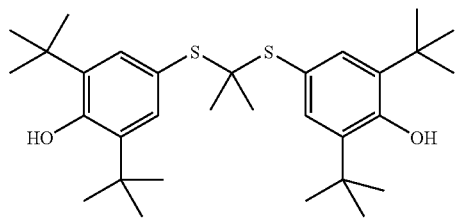

with a Grignard Reagent selected from the group consisting of alkylmagnesium halide, alkenylmagnesium halide, alkynylmagnesium halide, all of which may optionally be substituted by one or more selected from the group consisting of protected hydroxy, alkyl, alkenyl, protected acyl, nitro, protected amino, halo and protected carboxy, to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In an 8th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a solution of a compound of Formula IV with a Grignard Reagent selected from the group consisting of Methylmagnesium bromide; Octadecylmagnesium chloride; Tetradecylmagnesium chloride; n-Pentadecylmagnesium bromide; Ethynylmagnesium chloride; n-Nonylmagnesium bromide; n-Octylmagnesium chloride; (2-Methylpropenyl) magnesium bromide; Cyclopentylmagnesium bromide; tert-Pentyl magnesium chloride; Cyclopropylmagnesium bromide; (1-Methyl-2-propenyl)magnesium chloride; 1-Decylmagnesium bromide; 1-Octylmagnesium bromide; 1-Propynylmagnesium bromide; Dodecylmagnesium bromide; sec-Butylmagnesium chloride; 1-Propenylmagnesium bromide; Isopropenylmagnesium bromide; (2,2-Dimethylpropyl)magnesium chloride; 1-Heptylmagnesium bromide; 3-Butenylmagnesium bromide; 1-Pentylmagnesium chloride; 2-Methylpropylmagnesium chloride; (2-Methyl-2-propenyl)magnesium chloride; Ethynylmagnesium bromide; 1-Hexylmagnesium bromide; Vinylmagnesium chloride; Allylmagnesium chloride; Ethylmagnesium chloride; n-Propylmagnesium chloride; Vinylmagnesium bromide; Allylmagnesium bromide; Isopropylmagnesium chloride; Isopropylmagnesium bromide; Cyclohexylmagnesium chloride; Cyclohexylmagnesium bromide; 1-Propylmagnesium bromide; Isobutylmagnesium bromide; Ethylmagnesium bromide; 2-Butylmagnesium bromide; 2-Propylmagnesium bromide; Methylmagnesium iodide; n-Butylmagnesium chloride; n-Butylmagnesium bromide; tert-Butylmagnesium chloride; and Methylmagnesium chloride to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 9th embodiment, the invention is represented by the process of the 8th embodiment wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a solution of a compound of Formula IV with a Grignard Reagent selected from the group consisting of Methylmagnesium bromide; Octadecylmagnesium chloride; Tetradecylmagnesium chloride; n-Nonylmagnesium bromide; n-Octylmagnesium chloride; (2-Methylpropenyl)magnesium bromide; Cyclopentylmagnesium bromide; tert-Pentyl magnesium chloride; Cyclopropylmagnesium bromide; 1-Decylmagnesium bromide; 1-Octylmagnesium bromide; Dodecylmagnesium bromide; sec-Butylmagnesium chloride; (2,2-Dimethylpropyl)magnesium chloride; 1-Heptylmagnesium bromide; 1-Pentylmagnesium chloride; 2-Methylpropylmagnesium chloride; 1-Hexylmagnesium bromide; Ethylmagnesium chloride; n-Propylmagnesium chloride; Isopropylmagnesium chloride; Isopropylmagnesium bromide; Cyclohexylmagnesium chloride; Cyclohexylmagnesium bromide; 1-Propylmagnesium bromide; Isobutylmagnesium bromide; Ethylmagnesium bromide; 2-Butylmagnesium bromide; 2-Propylmagnesium bromide; Methylmagnesium iodide; n-Butylmagnesium chloride; n-Butylmagnesium bromide; tert-Butylmagnesium chloride; and Methylmagnesium chloride to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 10th embodiment, the invention is represented by the process of the 9th embodiment wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a solution of a compound of Formula IV with a Grignard Reagent selected from the group consisting of Methylmagnesium bromide; n-Octylmagnesium chloride; (2-Methylpropenyl)magnesium bromide; Cyclopentylmagnesium bromide; tert-Pentyl magnesium chloride; Cyclopropylmagnesium bromide; 1-Octylmagnesium bromide; sec-Butylmagnesium chloride; (2,2-Dimethylpropyl)magnesium chloride; 1-Heptylmagnesium bromide; 1-Pentylmagnesium chloride; 2-Methylpropylmagnesium chloride; 1-Hexylmagnesium bromide; Ethylmagnesium chloride; n-Propylmagnesium chloride; Isopropylmagnesium chloride; Isopropylmagnesium bromide; Cyclohexylmagnesium chloride; Cyclohexylmagnesium bromide; 1-Propylmagnesium bromide; Isobutylmagnesium bromide; Ethylmagnesium bromide; 2-Butylmagnesium bromide; 2-Propylmagnesium bromide; Methylmagnesium iodide; n-Butylmagnesium chloride; n-Butylmagnesium bromide; tert-Butylmagnesium chloride; and Methylmagnesium chloride to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In an 11th embodiment, the invention is represented by the process of the 10th embodiment wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a solution of a compound of Formula IV with a Grignard Reagent selected from the group consisting of n-Octylmagnesium chloride; (2-Methylpropenyl)magnesium bromide; Ethylmagnesium chloride; n-Propylmagnesium chloride; Isopropylmagnesium chloride;

Isopropylmagnesium bromide; Cyclohexylmagnesium chloride; Methylmagnesium iodide; n-Butylmagnesium chloride; tert-Butylmagnesium chloride; and Methylmagnesium chloride to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 12th embodiment, the invention is represented by the process of the 11th embodiment wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a solution of a compound of Formula IV with isopropylmagnesium chloride to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 13th embodiment, the invention is represented by the process of the 12th embodiment wherein:

X is hydrogen;

Y is a saturated acyl having from 1 to 10 carbon atoms or an optionally substituted saturated acyl having from 1 to 10 carbon atoms, said saturated acyl and optionally substituted saturated acyl optionally containing a polar or charged functionality; comprising:

reacting a solution of a compound of Formula IV with isopropylmagnesium chloride to form a magnesium salt;

reacting said magnesium salt with a compound selected from the group consisting of succinic acid anhydride, glutaric acid anhydride and acetic acid anhydride, all of which may optionally be substituted by one or more selected from the group consisting of protected hydroxy, alkyl, alkenyl, acyl, nitro, protected amino, halo, protected carboxy and cyano;

separating and isolating said compound of Formula III or salts thereof.

In a 14th embodiment, the invention is represented by the process of the 13th embodiment to manufacture a compound of Formula V or salts thereof

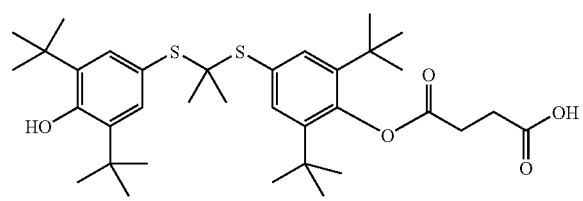

comprising:

reacting a solution of a compound of Formula IV with isopropylmagnesium chloride to form a magnesium salt;

reacting said magnesium salt with succinic acid anhydride; separating and isolating said compound of Formula V or salts thereof.

In a 15th embodiment, the invention is represented by the process of the 13th embodiment to manufacture a compound of Formula VI or salts thereof

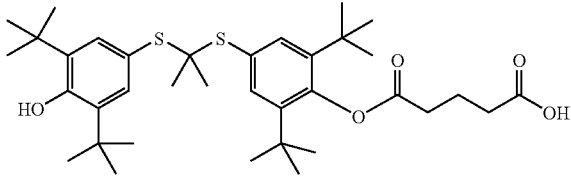

VI comprising:

reacting a compound of Formula IV with isopropylmagnesium chloride to form a magnesium salt;

reacting said magnesium salt with glutaric acid anhydride;

separating and isolating said compound of Formula VI or salts thereof.

In a 16th embodiment, the invention is represented by the process of the 13th embodiment to manufacture a compound of Formula VII or salts thereof

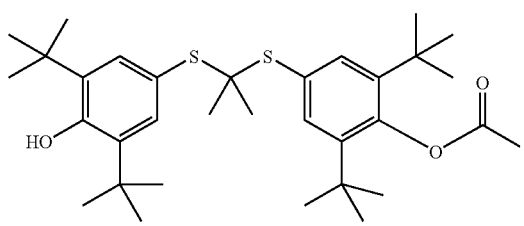

VII comprising:

reacting a compound of Formula IV with isopropylmagnesium chloride to form a magnesium salt;

reacting said magnesium salt with acetic acid anhydride;

separating and isolating said compound of Formula VII or salts thereof.

In a 17th embodiment, the invention is represented by the process of the 13th embodiment to manufacture a compound of Formula VIII or salts thereof

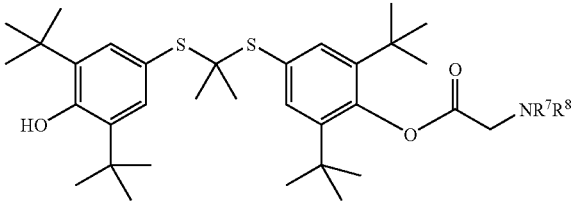

VIII wherein $R^7$ and $R^8$ are independently selected from the group consisting of hydrogen, acyl, alkyl, alkenyl, aryl, aralkyl, Si(alkyl)$_3$, protected carboxy, alksulfonyl, and arylsulfonyl comprising:

reacting a compound of Formula IV with isopropylmagnesium chloride to form a magnesium salt;

reacting said magnesium salt with acetic acid anhydride substituted by a protected or unprotected amino;

separating and isolating said compound of Formula VIII or salts thereof

In an 18th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

comprising:

reacting a solution of a compound of Formula IV with a Grignard Reagent selected from arylmagnesium halide or heteroarylmagnesium halide to form a magnesium salt, wherein said arylmagnesium halide and heteroarylmagnesium halide may optionally be substituted by one or more selected from the group consisting of protected hydroxy, alkyl, alkenyl, protected acyl, nitro, protected amino, halo and protected carboxy; reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 19th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of 3-Chloro-4-fluorophenylmagnesium bromide; 3-Fluoro-2-methylphenylmagnesium bromide; 5-Fluoro-2-methoxyphenylmagnesium bromide; 5-Fluoro-2-methylphenylmagnesium bromide; 3,5-Dimethyl-4-methoxyphenylmagnesium bromide; 3-Fluoro-4-methylphenylmagnesium bromide; 3-[Bis(trimethylsilyl)amino]phenylmagnesium chloride; 3-Thienylmagnesium iodide; 3-Fluoro-4-chlorophenylmagnesium bromide; 3,4,5-Trifluorophenylmagnesium bromide; 4-Methoxy-2-methylphenylmagnesium bromide; 2,4-Dimethoxyphenylmagnesium bromide; 2,3-Dimethylphenylmagnesium bromide; 3-Methylphenylmagnesium chloride; (4-methyl-1-naphthalenyl)magnesium bromide; (3-fluoro-4-methoxyphenyl)magnesium bromide; 2-Chloro-5-thienylmagnesium bromide; 3,4-Dimethylphenylmagnesium chloride; 3-Methyl-2-thienylmagnesium bromide; Pentamethylphenylmagnesium bromide; 3,4-Dimethoxyphenylmagnesium bromide; (3,4-Dimethylphenyl)magnesium bromide; (3,5-Dichlorophenyl)magnesium bromide; (4-Fluoro-3-methylphenyl)magnesium bromide; 3,4-Dichlorophenylmagnesium bromide; 2,3,5,6-

Tetramethylphenylmagnesium bromide; 9-Phenanthryl magnesium bromide; (4-tert-Butylphenyl)magnesium bromide; 2,5-Dimethoxyphenylmagnesium bromide; 3,5-Difluorophenylmagnesium bromide; 4-Chlorophenylmagnesium chloride; (6-Methoxy-2-naphthyl)magnesium bromide; (2-Methoxy-1-naphthyl)magnesium bromide; 3-Methoxyphenylmagnesium bromide; (3-Chlorophenyl)magnesium bromide; (3,5-Dimethylphenyl)magnesium bromide; (2-Methylphenyl)magnesium chloride; 4-Fluoro-2-methylphenylmagnesium bromide; (2,5-Dimethylphenyl)magnesium bromide; m-Methylphenylmagnesium bromide; 4-Ethylphenylmagnesium bromide; 2-Pyridylmagnesium bromide; 4-Phenoxyphenylmagnesium bromide; 2-Naphthylmagnesium bromide; (2-Methyl-1-naphthyl)magnesium bromide; 2,6-Dimethylphenylmagnesium bromide; 2-Ethylphenylmagnesium bromide; 4-(Methylthio)phenylmagnesium bromide; (4-Isopropylphenyl)magnesium bromide; 3,4-Methylenedioxyphenylmagnesium bromide; 3-Fluorophenylmagnesium bromide; (o-Methoxyphenyl)magnesium bromide; Phenylmagnesium iodide; (4-Methoxyphenyl)magnesium bromide; 4-(Dimethylamino)phenylmagnesium bromide; 2-Thienylmagnesium bromide; (4-Methylphenyl)magnesium bromide; Mesitymagnesium bromide; 2-Tolylmagnesium bromide; Pentafluorophenylmagnesium bromide; (4-Chlorophenyl)magnesium bromide; 1-Naphthalenylmagnesium bromide; 4-Methylphenylmagnesium chloride; 4-Fluorophenylmagnesium bromide; Phenylmagnesium chloride; Phenylmagnesium bromide; and (4-Biphenylyl)magnesium bromide to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 20$^{th}$ embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of 3,5-Dimethyl-4-methoxyphenylmagnesium bromide; 4-Methoxy-2-methylphenylmagnesium bromide; 2,4-Dimethoxyphenylmagnesium bromide; 2,3-Dimethylphenylmagnesium bromide; 3-Methylphenylmagnesium chloride; 3,4-Dimethylphenylmagnesium chloride; Pentamethylphenylmagnesium bromide; 3,4-Dimethoxyphenylmagnesium bromide; (3,4-Dimethylphenyl)magnesium bromide; 2,3,5,6-Tetramethylphenylmagnesium bromide; (4-tert-Butylphenyl)magnesium bromide; 2,5-Dimethoxyphenylmagnesium bromide; 3-Methoxyphenylmagnesium bromide; (3,5-Dimethylphenyl)magnesium bromide; (2-Methylphenyl)magnesium chloride; (2,5-Dimethylphenyl)magnesium bromide; m-Methylphenylmagnesium bromide; 4-Ethylphenylmagnesium bromide; 4-Phenoxyphenylmagnesium bromide; 2,6-Dimethylphenylmagnesium bromide; 2-Ethylphenylmagnesium bromide; (4-Isopropylphenyl)magnesium bromide; 3,4-Methylenedioxyphenylmagnesium bromide; (o-Methoxyphenyl)magnesium bromide; Phenylmagnesium iodide; (4-Methoxyphenyl)magnesium bromide; (4-Methylphenyl) magnesium bromide; Mesitymagnesium bromide; 2-Tolylmagnesium bromide; 4-Methylphenylmagnesium chloride; Phenylmagnesium chloride; and Phenylmagnesium bromide to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 21$^{st}$ embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of 3-Methylphenylmagnesium chloride; (4-tert-Butylphenyl)magnesium bromide; 3-Methoxyphenylmagnesium bromide; (2-Methylphenyl) magnesium chloride; m-Methylphenylmagnesium bromide; 4-Ethylphenylmagnesium bromide; 2-Ethylphenylmagnesium bromide; (4-Isopropylphenyl)magnesium bromide; (o-Methoxyphenyl)magnesium bromide; Phenylmagnesium iodide; (4-Methoxyphenyl)magnesium bromide; (4-Methylphenyl)magnesium bromide; 2-Tolylmagnesium bromide; 4-Methylphenylmagnesium chloride; Phenylmagnesium chloride; and Phenylmagnesium bromide to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 22$^{nd}$ embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

comprising:

reacting a compound of Formula IV with a Grignard Reagent selected from the group consisting of 3-Methylphenylmagnesium chloride; 3-Methoxyphenylmagnesium bromide; (2-Methylphenyl)magnesium chloride; m-Methylphenylmagnesium bromide; (o-Methoxyphenyl)magnesium bromide; Phenylmagnesium iodide; (4-Methoxyphenyl)magnesium bromide; (4-Methylphenyl)magnesium bromide; 2-Tolylmagnesium bromide; 4-Methylphenylmagnesium chloride; Phenylmagnesium chloride; and Phenylmagnesium bromide to form a magnesium salt; reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 23$^{rd}$ embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 24$^{th}$ embodiment, the invention is represented by the process to manufacture a compound of Formula III or salts thereof wherein:

X is hydrogen;

Y is a saturated acyl having from 1 to 10 carbon atoms or an optionally substituted saturated acyl having from 1 to 10 carbon atoms, said saturated acyl and optionally substituted saturated acyl optionally containing a polar or charged functionality; comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with a compound selected from the group consisting of succinic acid anhydride, glutaric acid anhydride and acetic acid anhydride, all of which may optionally be substituted by one or more selected from the group consisting of protected hydroxy, alkyl, alkenyl, acyl, nitro, protected amino, halo, protected carboxy and cyano;

separating and isolating said compound of Formula III or salts thereof.

In a 25$^{th}$ embodiment, the invention is represented by the process to manufacture a compound of Formula V or salts thereof

comprising:

reacting a solution of a compound of Formula IV

with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with succinic acid anhydride;

separating and isolating said compound of Formula V or salts thereof.

In a 26$^{th}$ embodiment, the invention is represented by the process to manufacture a compound of Formula VI or salts thereof

comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with glutaric acid anhydride;

separating and isolating said compound of Formula VI or salts thereof.

In a 27th embodiment, the invention is represented by the process to manufacture a compound of Formula VII or salts thereof

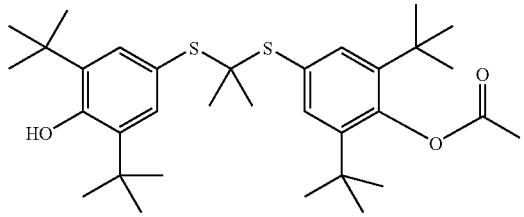

VII comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with acetic acid anhydride;

separating and isolating said compound of Formula VII or salts thereof.

In a 28th embodiment, the invention is represented by the process to manufacture a compound of Formula VIII or salts thereof

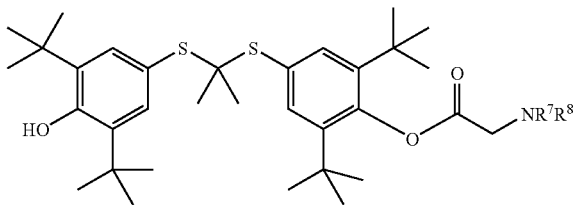

VIII wherein $R^7$ and $R^8$ are independently selected from the group consisting of hydrogen, acyl, alkyl, alkenyl, aryl, aralkyl, Si(alkyl)$_3$, protected carboxy, alksulfonyl, and arylsulfonyl;

comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with acetic acid anhydride substituted by a protected or unprotected amino;

separating and isolating said compound of Formula VIII or salts thereof

In a 29th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

comprising:

reacting a compound of Formula IV with a Grignard Reagent selected from the group consisting of arylalkylmagnesium halide, arylalkynylmagnesium halide, and arylalkenylmagnesium halide to form a magnesium salt, all of which may optionally be substituted by one or more selected from the group consisting of protected hydroxy, alkyl, alkenyl, protected acyl, nitro, protected amino, halo and protected carboxy; reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 30th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of 2,5-Dimethylbenzylmagnesium chloride; 2,6-Dichlorobenzylmagnesium chloride; 2,4-Dichlorobenzylmagnesium chloride; 2-Fluorobenzylmagnesium chloride; 2,4-Dimethylbenzylmagnesium chloride; 3-Bromobenzylmagnesium bromide; 4-Bromobenzylmagnesium bromide; (2-Phenylethyl)magnesium chloride; 3-Fluorobenzylmagnesium chloride; (3,4-Dichlorobenzyl)magnesium chloride; 2-Bromobenzylmagnesium bromide; 4-Methoxybenzylmagnesium chloride; 4-Methylbenzylmagnesium chloride; m-Methylbenzylmagnesium chloride; 2-Methylbenzylmagnesium chloride; 3-Chlorobenzylmagnesium chloride; 2-Chlorobenzylmagnesium chloride; m-Methoxybenzylmagnesium chloride; Benzylmagnesium chloride; (Phenylethynyl)magnesium bromide; 4-Fluorobenzylmagnesium chloride; Benzylmagnesium bromide; 4-Chlorobenzylmagnesium chloride; and 2-Chloro-6-fluorobenzylmagnesium chloride to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 31st embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of 2,5-Dimethylbenzylmagnesium chloride; 2,4-Dimethylbenzylmagnesium chloride; (2-Phenylethyl)magnesium chloride; 4-Methoxybenzylmagnesium chloride; 4-Methylbenzylmagnesium chloride; m-Methylbenzylmagnesium chloride; 2-Methylbenzylmagnesium chloride; m-Methoxybenzylmagnesium chloride; Benzylmagnesium chloride; and Benzylmagnesium bromide to form a magnesium salt; reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 32$^{nd}$ embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with Benzylmagnesium chloride to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 33$^{rd}$ embodiment, the invention is represented by the process to manufacture a compound of Formula III or salts thereof wherein:

X is hydrogen;

Y is a saturated acyl having from 1 to 10 carbon atoms or an optionally substituted saturated acyl having from 1 to 10 carbon atoms, said saturated acyl and optionally substituted saturated acyl optionally containing a polar or charged functionality; comprising:

reacting a solution of a compound of Formula IV with Benzylmagnesium chloride to form a magnesium salt;

reacting said magnesium salt with a compound selected from the group consisting of succinic acid anhydride, glutaric acid anhydride and acetic acid anhydride, all of which may optionally be substituted by one or more selected from the group consisting of protected hydroxy, alkyl, alkenyl, acyl, nitro, protected amino, halo, protected carboxy and cyano;

separating and isolating said compound of Formula III or salts thereof.

In a 34$^{th}$ embodiment, the invention is represented by the process to manufacture a compound of Formula V or salts thereof

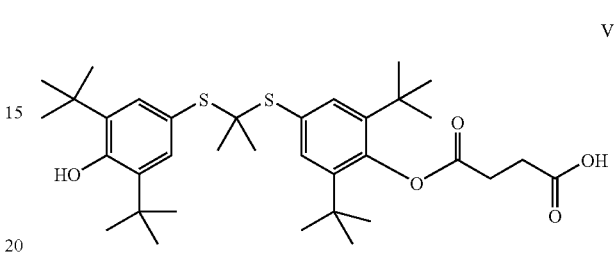

comprising:

reacting a compound of Formula IV with Benzylmagnesium chloride to form a magnesium salt;

reacting said magnesium salt with succinic acid anhydride;

separating and isolating said compound of Formula V or salts thereof.

In a 35$^{th}$ embodiment, the invention is represented by the process to manufacture a compound of Formula VI or salts thereof

VI

HO—(structure shown)

comprising:

reacting a compound of Formula IV with Benzylmagnesium chloride to form a magnesium salt;

reacting said magnesium salt with glutaric acid anhydride;

separating and isolating said compound of Formula VI or salts thereof.

In a 36$^{th}$ embodiment, the invention is represented by the process to manufacture a compound of Formula VII or salts thereof

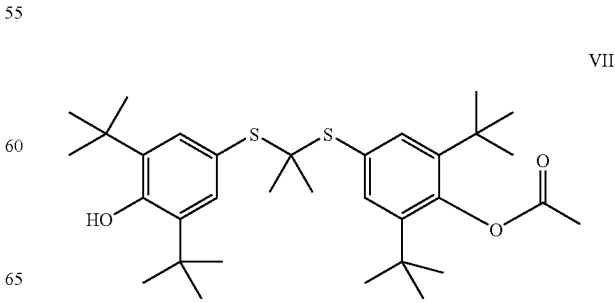

comprising:

reacting a compound of Formula IV with Benzylmagnesium chloride to form a magnesium salt;

reacting said magnesium salt with acetic acid anhydride;

separating and isolating said compound of Formula VII or salts thereof.

In a 37th embodiment, the invention is represented by the process to manufacture a compound of Formula VIII or salts thereof

VIII

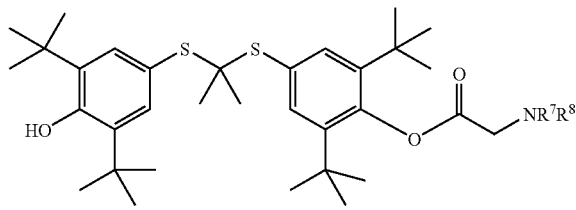

wherein $R^7$ and $R^8$ are independently selected from the group consisting of hydrogen, acyl, alkyl, alkenyl, aryl, aralkyl, $Si(alkyl)_3$, protected carboxy, alksulfonyl, and arylsulfonyl comprising:

reacting a compound of Formula IV with Benzylmagnesium chloride to form a magnesium salt;

reacting said magnesium salt with acetic acid anhydride substituted by a protected or unprotected amino;

separating and isolating said compound of Formula VIII or salts thereof

In a 38th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from alkylmagnesium alkyl or arylmagnesium aryl to form a magnesium salt, wherein said alkylmagnesium alkyl and arylmagnesium aryl may optionally be substituted by one or more selected from the group consisting of protected hydroxy, alkyl, alkenyl, protected acyl, nitro, protected amino, halo and protected carboxy;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 39th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more selected from the group consisting of protected hydroxy, alkyl, alkenyl, acyl, nitro, protected amino, halo, protected carboxy and cyano; separating and isolating said compound of Formula III or salts thereof.

In a 40th embodiment, the invention is represented by the process to manufacture a compound of Formula III or salts thereof wherein:

X is hydrogen;

Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with a compound selected from the group consisting of succinic acid anhydride, glutaric acid anhydride and acetic acid anhydride, all of which may optionally be substituted by one or more selected from the group consisting of protected hydroxy, alkyl, alkenyl, acyl, nitro, protected amino, halo, protected carboxy and cyano;

separating and isolating said compound of Formula III or salts thereof.

In a 41st embodiment, the invention is represented by the process to manufacture a compound of Formula V or salts thereof

V

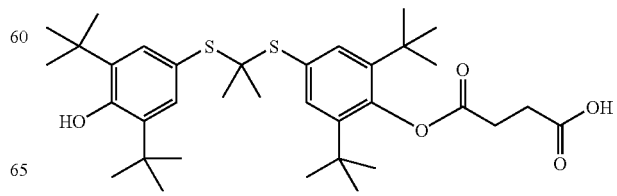

comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with succinic acid anhydride;

separating and isolating said compound of Formula V or salts thereof.

In a 42nd embodiment, the invention is represented by the process to manufacture a compound of Formula VI or salts thereof

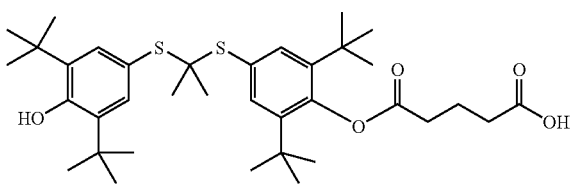

VI comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with glutaric acid anhydride;

separating and isolating said compound of Formula VI or salts thereof.

In a 43$^{rd}$ embodiment, the invention is represented by the process to manufacture a compound of Formula VII or salts thereof

VII

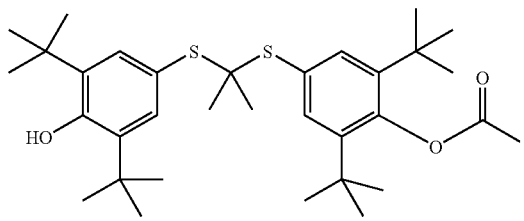

comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with acetic acid anhydride;

separating and isolating said compound of Formula VII or salts thereof.

In a 44$^{th}$ embodiment, the invention is represented by the process to manufacture a compound of Formula VIII or salts thereof

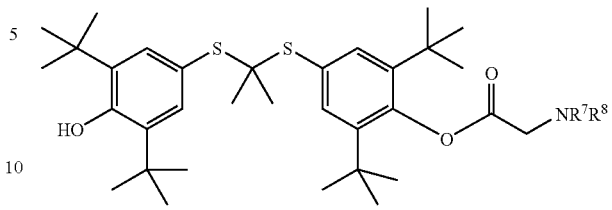

VIII wherein $R^7$ and $R^8$ are independently selected from the group consisting of hydrogen, acyl, alkyl, alkenyl, aryl, aralkyl, Si(alkyl)$_3$, protected carboxy, alksulfonyl, and arylsulfonyl comprising:

reacting a compound of Formula IV with a Grignard Reagent selected from the group consisting of n-Butyl-sec-butylmagnesium; Dimethylmagnesium; Di-n-Butylmagnesium; Diethylmagnesium and Diphenylmagnesium to form a magnesium salt;

reacting said magnesium salt with acetic acid anhydride substituted by a protected or unprotected amino;

separating and isolating said compound of Formula VIII or salts thereof

In a 45$^{th}$ embodiment, the invention is represented by the process to manufacture a compound of Formula I or salts thereof

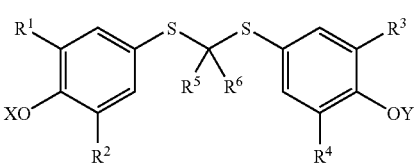

I wherein $R^1$, $R^2$, $R^3$, and $R^4$ are independently selected from the group consisting of hydrogen and alkyl, said alkyl optionally substituted by hydroxy, alkyl, alkenyl, acyl, nitro, amino, halo, carboxy and cyano;

$R^5$ and $R^6$ are the same or different and independently selected from the group consisting of alkyl, alkenyl, and aryl all of which can be optionally substituted by hydroxy, alkyl, alkenyl, acyl, nitro, amino, halo, carboxy and cyano;

$R^5$ and $R^6$ can come together to form a carbocyclic ring; X is selected from the group consisting of hydrogen, an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula II

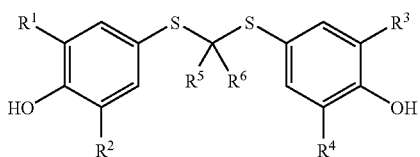

wherein $R^1$, $R^2$, $R^3$, $R^4$, $R^5$ and $R^6$ are as previously defined, with a Grignard Reagent to form a magnesium salt or a reagent selected from the group consisting of an alkyl lithium, alkenyl lithium, alkynyl lithium, aryl lithium, aralkyl lithium, and a heteroaryl lithium, all which can be optionally substituted to form a lithium salt;

reacting said magnesium salt or lithium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano; separating and isolating said compound of Formula I or salts thereof.

In a 46th embodiment, the invention is represented by the process to manufacture a compound of Formula III or salts thereof

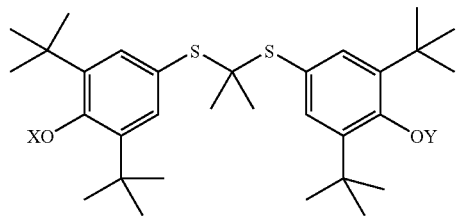

wherein:

X is selected from the group consisting of hydrogen, an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV

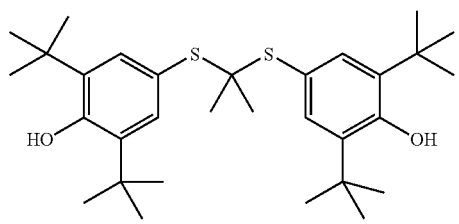

with a Grignard Reagent to form a magnesium salt or a reagent selected from the group consisting of an alkyl lithium, alkenyl lithium, alkynyl lithium, aryl lithium, aralkyl lithium, and a heteroaryl lithium, all which can be optionally substituted to form a lithium salt;

reacting said magnesium salt or lithium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano; separating and isolating said compound of Formula III or salts thereof.

In a 47th embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent to form a magnesium salt or a reagent selected from the group consisting of an alkyl lithium, alkenyl lithium, alkynyl lithium, aryl lithium, aralkyl lithium, and a heteroaryl lithium, all which can be optionally substituted to form a lithium salt;

reacting said magnesium salt or lithium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano; separating and isolating said compound of Formula III or salts thereof.

In a 48th embodiment, the invention is represented by the process to manufacture a compound of Formula III or salts thereof wherein:

X is selected from the group consisting of hydrogen, an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent to form a magnesium salt; reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 49th embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent to form a magnesium salt; reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 50$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of alkylmagnesium halide, alkenylmagnesium halide, alkynylmagnesium halide, arylmagnesium halide, arylalkylmagnesium halide, alkylmagnesium alkyl, arylmagnesium aryl, arylalkynylmagnesium halide, arylalkenylmagnesium halide, and heteroarylmagnesium halide, all of which may optionally be substituted by one or more selected from the group consisting of protected hydroxy, alkyl, alkenyl, protected acyl, nitro, protected amino, halo and protected carboxy, to form a magnesium salt;

reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 51$^{st}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a solution of a compound of Formula IV with a Grignard Reagent selected from the group consisting of alkylmagnesium halide, alkenylmagnesium halide, alkynylmagnesium halide, all of which may optionally be substituted by one or more selected from the group consisting of protected hydroxy, alkyl, alkenyl, protected acyl, nitro, protected amino, halo and protected carboxy, to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 52$^{nd}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a solution of a compound of Formula IV with a Grignard Reagent selected from the group consisting of Methylmagnesium bromide; Octadecylmagnesium chloride; Tetradecylmagnesium chloride; n-Pentadecylmagnesium bromide; Ethynylmagnesium chloride; n-Nonylmagnesium bromide; n-Octylmagnesium chloride; (2-Methylpropenyl)magnesium bromide; Cyclopentylmagnesium bromide; tert-Pentyl magnesium chloride; Cyclopropylmagnesium bromide; (1-Methyl-2-propenyl)magnesium chloride; 1-Decylmagnesium bromide; 1-Octylmagnesium bromide; 1-Propynylmagnesium bromide; Dodecylmagnesium bromide; sec-Butylmagnesium chloride; 1-Propenylmagnesium bromide; Isopropenylmagnesium bromide; (2,2-Dimethylpropyl)magnesium chloride; 1-Heptylmagnesium bromide; 3-Butenylmagnesium bromide; 1-Pentylmagnesium chloride; 2-Methylpropylmagnesium chloride; (2-Methyl-2-propenyl)magnesium chloride; Ethynylmagnesium bromide; 1-Hexylmagnesium bromide; Vinylmagnesium chloride; Allylmagnesium chloride; Ethylmagnesium chloride; n-Propylmagnesium chloride; Vinylmagnesium bromide; Allylmagnesium bromide; Isopropylmagnesium chloride; Isopropylmagnesium bromide; Cyclohexylmagnesium chloride; Cyclohexylmagnesium bromide; 1-Propylmagnesium bromide; Isobutylmagnesium bromide; Ethylmagnesium bromide; 2-Butylmagnesium bromide; 2-Propylmagnesium bromide; Methylmagnesium iodide; n-Butylmagnesium chloride; n-Butylmagnesium bromide; tert-Butylmagnesium chloride; and Methylmagnesium chloride to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 53$^{rd}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a solution of a compound of Formula IV with a Grignard Reagent selected from the group consisting of Methylmagnesium bromide; Octadecylmagnesium chloride; Tetradecylmagnesium chloride; n-Nonylmagnesium bromide; n-Octylmagnesium chloride; (2-Methylpropenyl)magnesium bromide; Cyclopentylmagnesium bromide; tert-Pentyl magnesium chloride; Cyclopropylmagnesium bromide; 1-Decylmagnesium bromide; 1-Octylmagnesium bromide; Dodecylmagnesium bromide; sec-Butylmagnesium chloride; (2,2-Dimethylpropyl)magnesium chloride; 1-Heptylmagnesium bromide; 1-Pentylmagnesium chloride; 2-Methylpropylmagnesium chloride; 1-Hexylmagnesium bromide; Ethylmagnesium chloride; n-Propylmagnesium chloride; Isopropylmagnesium chloride; Isopropylmagnesium bromide; Cyclohexylmagnesium chloride; Cyclohexylmagnesium bromide; 1-Propylmagnesium bromide; Isobutylmagnesium bromide; Ethylmagnesium bromide; 2-Butylmagnesium bromide; 2-Propylmagnesium bromide; Methylmagnesium iodide; n-Butylmagnesium chloride; n-Butylmagnesium bromide; tert-Butylmagnesium chloride; and Methylmagnesium chloride to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 54$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a solution of a compound of Formula IV with a Grignard Reagent selected from the group consisting of Methylmagnesium bromide; n-Octylmagnesium chloride; (2-Methylpropenyl)magnesium bromide; Cyclopentylmagnesium bromide; tert-Pentyl magnesium chloride; Cyclopropylmagnesium bromide; 1-Octylmagnesium bromide; sec-Butylmagnesium chloride; (2,2-Dimethylpropyl)magnesium chloride; 1-Heptylmagnesium bromide; 1-Pentylmagnesium chloride; 2-Methylpropylmagnesium chloride; 1-Hexylmagnesium bromide; Ethylmagnesium chloride; n-Propylmagnesium chloride; Isopropylmagnesium chloride; Isopropylmagnesium bromide; Cyclohexylmagnesium chloride; Cyclohexylmagnesium bromide; 1-Propylmagnesium bromide; Isobutylmagnesium bromide; Ethylmagnesium bromide; 2-Butylmagnesium bromide; 2-Propylmagnesium bromide; Methylmagnesium iodide; n-Butylmagnesium chloride; n-Butylmagnesium bromide; tert-Butylmagnesium chloride; and Methylmagnesium chloride to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 55$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a solution of a compound of Formula IV with a Grignard Reagent selected from the group consisting of n-Octylmagnesium chloride; (2-Methylpropenyl)magnesium bromide; Ethylmagnesium chloride; n-Propylmagnesium chloride; Isopropylmagnesium chloride; Isopropylmagnesium bromide; Cyclohexylmagnesium chloride; Methylmagnesium iodide; n-Butylmagnesium chloride; tert-Butylmagnesium chloride; and Methylmagnesium chloride to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 56$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a solution of a compound of Formula IV with isopropylmagnesium chloride to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 57$^{th}$ embodiment, the invention is represented by the process to manufacture a compound of Formula IX, X, XI or XII or salts thereof

IX

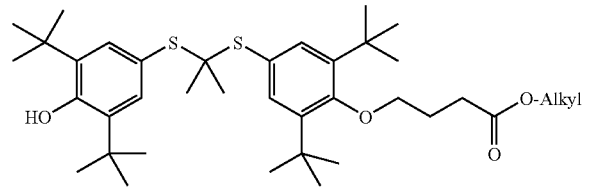

X

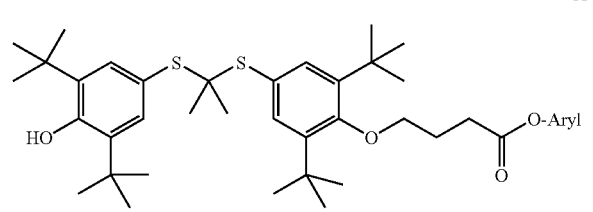

XI

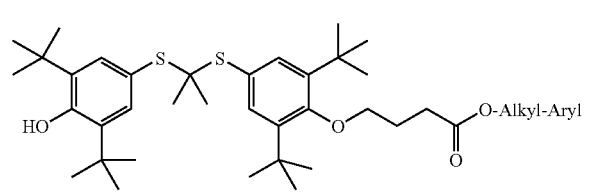

XII

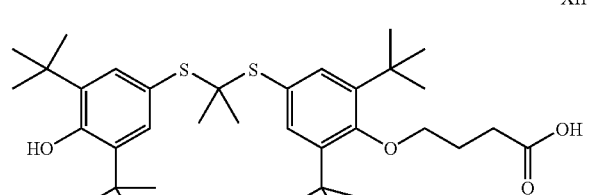

comprising:

reacting a solution of a compound of Formula IV with isopropylmagnesium chloride to form a magnesium salt;

reacting said magnesium salt with a compound selected from the group consisting of alkyl 4-halobutyrate, aryl 4-halobutyrate, aralkyl 4-halobutyrate, and butyrolactone; separating and isolating said compound of Formula IX, X, XI or XII or salts thereof.

In a 58$^{th}$ embodiment, the invention is represented by the process to manufacture a compound of Formula XIII, XIV, XV or XVI or salts thereof

XIII

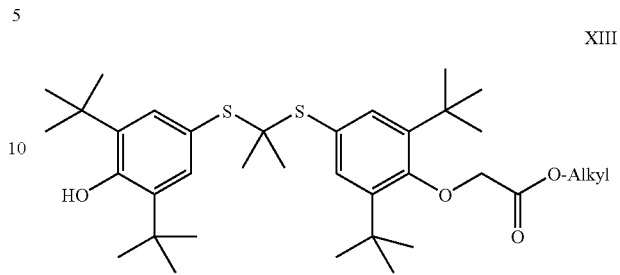

XIV

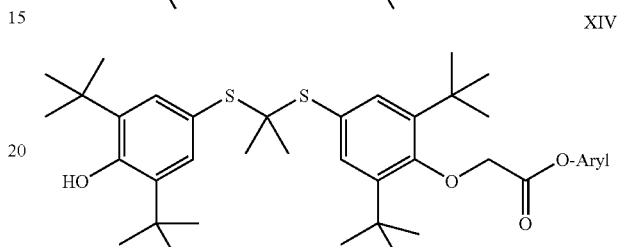

XV

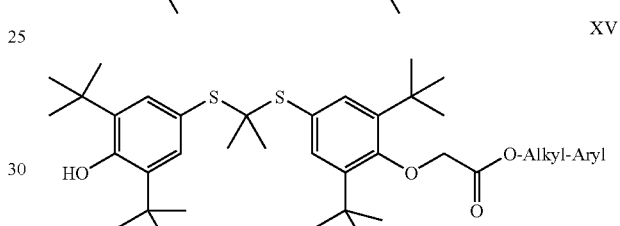

XVI

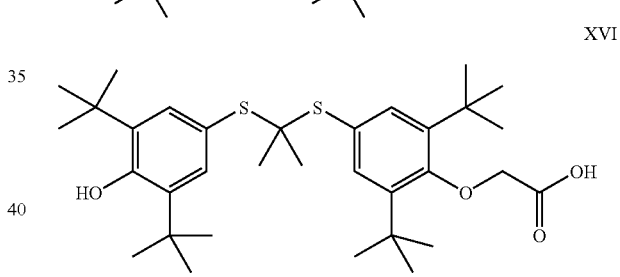

comprising:

reacting a compound of Formula IV with isopropylmagnesium chloride to form a magnesium salt;

reacting said magnesium salt with alkyl haloacetate, aryl haloacetate, aralkyl haloacetate, and alkali metal haloacetate;

separating and isolating said compound of Formula XIII, XIV, XV or XVI or salts thereof.

In a 59$^{th}$ embodiment, the invention is represented by the process to manufacture a compound of Formula XVII or salts thereof

XVII

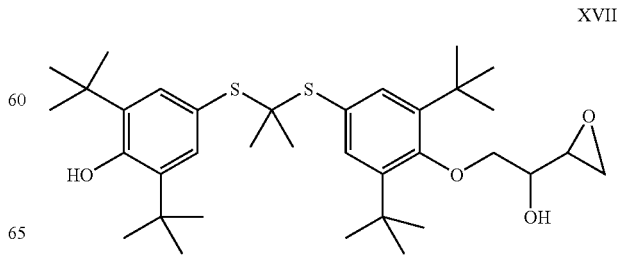

comprising:

reacting a compound of Formula IV with isopropylmagnesium chloride to form a magnesium salt;

reacting said magnesium salt with diepoxybutane;

separating and isolating said compound of Formula XVI or salts thereof.

In a 60$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a solution of a compound of Formula IV with a Grignard Reagent selected from arylmagnesium halide or heteroarylmagnesium halide to form a magnesium salt, wherein said arylmagnesium halide and heteroarylmagnesium halide may optionally be substituted by one or more selected from the group consisting of protected hydroxy, alkyl, alkenyl, protected acyl, nitro, protected amino, halo and protected carboxy; reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 61$^{st}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of 3-Chloro-4-fluorophenylmagnesium bromide; 3-Fluoro-2-methylphenylmagnesium bromide; 5-Fluoro-2-methoxyphenylmagnesium bromide; 5-Fluoro-2-methylphenylmagnesium bromide; 3,5-Dimethyl-4-methoxyphenylmagnesium bromide; 3-Fluoro-4-methylphenylmagnesium bromide; 3-[Bis(trimethylsilyl)amino]phenylmagnesium chloride; 3-Thienylmagnesium iodide; 3-Fluoro-4-chlorophenylmagnesium bromide; 3,4,5-Trifluorophenylmagnesium bromide; 4-Methoxy-2-methylphenylmagnesium bromide; 2,4-Dimethoxyphenylmagnesium bromide; 2,3-Dimethylphenylmagnesium bromide; 3-Methylphenylmagnesium chloride; (4-methyl-1-naphthalenyl)magnesium bromide; (3-fluoro-4-methoxyphenyl)magnesium bromide; 2-Chloro-5-thienylmagnesium bromide; 3,4-Dimethylphenylmagnesium chloride; 3-Methyl-2-thienylmagnesium bromide; Pentamethylphenylmagnesium bromide; 3,4-Dimethoxyphenylmagnesium bromide; (3,4-Dimethylphenyl)magnesium bromide; (3,5-Dichlorophenyl)magnesium bromide; (4-Fluoro-3-methylphenyl)magnesium bromide; 3,4-Dichlorophenylmagnesium bromide; 2,3,5,6-Tetramethylphenylmagnesium bromide; 9-Phenanthryl magnesium bromide; (4-tert-Butylphenyl)magnesium bromide; 2,5-Dimethoxyphenylmagnesium bromide; 3,5-Difluorophenylmagnesium bromide; 4-Chlorophenylmagnesium chloride; (6-Methoxy-2-naphthyl)magnesium bromide; (2-Methoxy-1-naphthyl)magnesium bromide; 3-Methoxyphenylmagnesium bromide; (3-Chlorophenyl)magnesium bromide; (3,5-Dimethylphenyl)magnesium bromide; (2-Methylphenyl)magnesium chloride; 4-Fluoro-2-methylphenylmagnesium bromide; (2,5-Dimethylphenyl)magnesium bromide; m-Methylphenylmagnesium bromide; 4-Ethylphenylmagnesium bromide; 2-Pyridylmagnesium bromide; 4-Phenoxyphenylmagnesium bromide; 2-Naphthylmagnesium bromide; (2-Methyl-1-naphthyl)magnesium bromide; 2,6-Dimethylphenylmagnesium bromide; 2-Ethylphenylmagnesium bromide; 4-(Methylthio)phenylmagnesium bromide; (4-Isopropylphenyl)magnesium bromide; 3,4-Methylenedioxyphenylmagnesium bromide; 3-Fluorophenylmagnesium bromide; (o-Methoxyphenyl)magnesium bromide; Phenylmagnesium iodide; (4-Methoxyphenyl)magnesium bromide; 4-(Dimethylamino)phenylmagnesium bromide; 2-Thienylmagnesium bromide; (4-Methylphenyl)magnesium bromide; Mesitymagnesium bromide; 2-Tolylmagnesium bromide; Pentafluorophenylmagnesium bromide; (4-Chlorophenyl)magnesium bromide; 1-Naphthalenylmagnesium bromide; 4-Methylphenylmagnesium chloride; 4-Fluorophenylmagnesium bromide; Phenylmagnesium chloride; Phenylmagnesium bromide; and (4-Biphenylyl)magnesium bromide to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 62$^{nd}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of 3,5-Dimethyl-4-methoxyphenylmagnesium bromide; 4-Methoxy-2-methylphenylmagnesium bromide; 2,4-Dimethoxyphenylmagnesium bromide; 2,3-Dimethylphenylmagnesium bromide; 3-Methylphenylmagnesium chloride; 3,4-Dimethylphenylmagnesium chloride; Pentamethylphenylmagnesium bromide; 3,4-Dimethoxyphenylmagnesium bromide; (3,4-Dimethylphenyl)magnesium bromide; 2,3,5,6-Tetramethylphenylmagnesium bromide; (4-tert-Butylphenyl)magnesium bromide; 2,5-Dimethoxyphenylmagnesium bromide;

3-Methoxyphenylmagnesium bromide; (3,5-Dimethylphenyl)magnesium bromide; (2-Methylphenyl)magnesium chloride; (2,5-Dimethylphenyl)magnesium bromide; m-Methylphenylmagnesium bromide; 4-Ethylphenylmagnesium bromide; 4-Phenoxyphenylmagnesium bromide; 2,6-Dimethylphenylmagnesium bromide; 2-Ethylphenylmagnesium bromide; (4-Isopropylphenyl)magnesium bromide; 3,4-Methylenedioxyphenylmagnesium bromide; (o-Methoxyphenyl)magnesium bromide; Phenylmagnesium iodide; (4-Methoxyphenyl)magnesium bromide; (4-Methylphenyl) magnesium bromide; Mesitymagnesium bromide; 2-Tolylmagnesium bromide; 4-Methylphenylmagnesium chloride; Phenylmagnesium chloride; and Phenylmagnesium bromide to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 63$^{rd}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of 3-Methylphenylmagnesium chloride; (4-tert-Butylphenyl)magnesium bromide; 3-Methoxyphenylmagnesium bromide; (2-Methylphenyl) magnesium chloride; m-Methylphenylmagnesium bromide; 4-Ethylphenylmagnesium bromide; 2-Ethylphenylmagnesium bromide; (4-Isopropylphenyl)magnesium bromide; (o-Methoxyphenyl)magnesium bromide; Phenylmagnesium iodide; (4-Methoxyphenyl)magnesium bromide; (4-Methylphenyl)magnesium bromide; 2-Tolylmagnesium bromide; 4-Methylphenylmagnesium chloride; Phenylmagnesium chloride; and Phenylmagnesium bromide to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 64$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of 3-Methylphenylmagnesium chloride; 3-Methoxyphenylmagnesium bromide; (2-Methylphenyl)magnesium chloride; m-Methylphenylmagnesium bromide; (o-Methoxyphenyl)magnesium bromide; Phenylmagnesium iodide; (4-Methoxyphenyl)magnesium bromide; (4-Methylphenyl)magnesium bromide; 2-Tolylmagnesium bromide; 4-Methylphenylmagnesium chloride; Phenylmagnesium chloride; and Phenylmagnesium bromide to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 65$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 66$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with a compound selected from the group consisting of alkyl 4-halobutyrate, aryl 4-halobutrate, aralkyl 4-halobutyrate, butyrolactone, alkyl haloacetate, aryl haloacetate, aralkyl haloacetate, and diepoxybutane, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 67$^{th}$ embodiment, the invention is represented by the process to manufacture a compound of Formula IX, X, XI or XII or salts thereof

IX

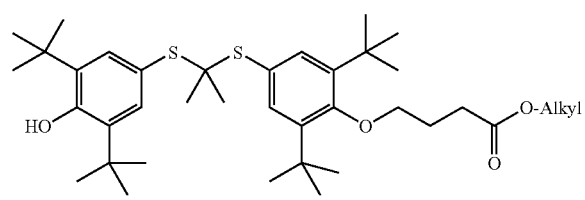

X

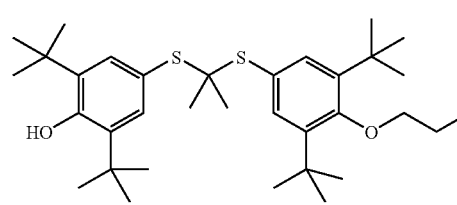

XI

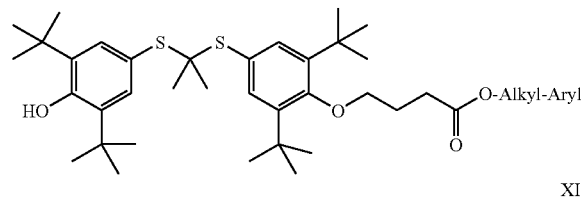

XII

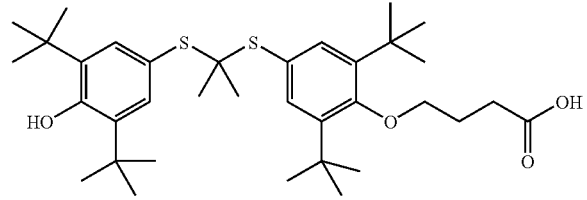

comprising:

reacting a solution of a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with a compound from the group consisting of alkyl 4-halobutyrate, aryl 4-halobutyrate, aralkyl 4-halobutyrate, and butyrolactone;

separating and isolating said compound of Formula IX, X, XI or XII or salts thereof.

In a 68$^{th}$ embodiment, the invention is represented by the process to manufacture a compound of Formula XIII, XIV, XV or XVI or salts thereof

XIII

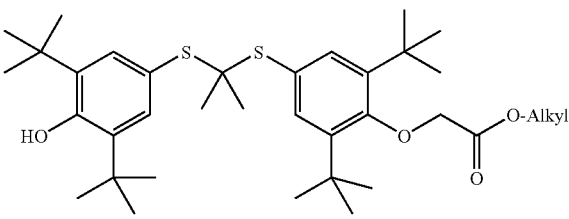

XIV

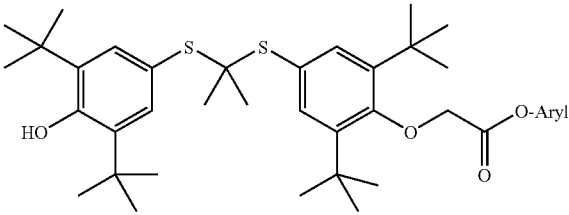

XV

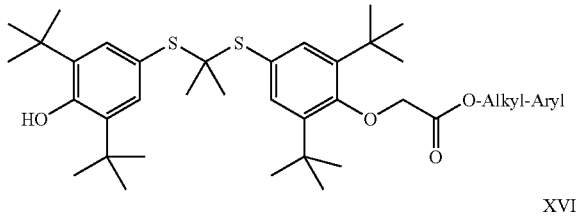

XVI

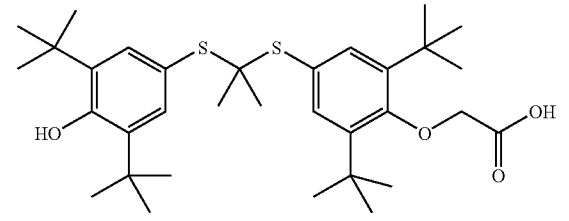

comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with alkyl haloacetate, aryl haloacetate, aralkyl haloacetate, and alkali metal haloacetate;

separating and isolating said compound of Formula XIII, XIV, XV or XVI or salts thereof.

In a 69$^{th}$ embodiment, the invention is represented by the process to manufacture a compound of Formula XVII or salts thereof

XVII

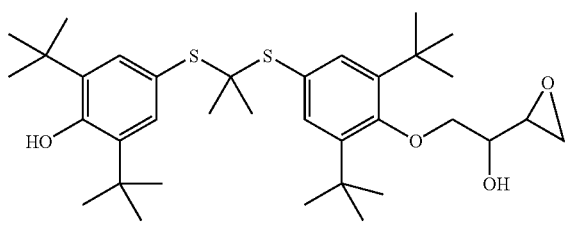

comprising:

reacting a compound of Formula IV with a Grignard Reagent selected from the group consisting of 3-Methoxyphenylmagnesium bromide; (o-Methoxyphenyl)magnesium bromide; and Phenylmagnesium chloride to form a magnesium salt;

reacting said magnesium salt with diepoxybutane;

separating and isolating said compound of Formula XVII or salts thereof.

In a 70$^{th}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of arylalkylmagnesium halide, arylalkynylmagnesium halide, and arylalkenylmagnesium halide to form a magnesium salt, all of which may optionally be substituted by one or more selected from the group consisting of protected hydroxy, alkyl, alkenyl, protected acyl, nitro, protected amino, halo and protected carboxy; reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 71$^{st}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of 2,5-Dimethylbenzylmagnesium chloride; 2,6-Dichlorobenzylmagnesium chloride; 2,4-Dichlorobenzylmagnesium chloride; 2-Fluorobenzylmagnesium chloride; 2,4-Dimethylbenzylmagnesium chloride; 3-Bromobenzylmagnesium bromide; 4-Bromobenzylmagnesium bromide; (2-Phenylethyl)magnesium chloride; 3-Fluorobenzylmagnesium chloride; (3,4-Dichlorobenzyl)magnesium chloride; 2-Bromobenzylmagnesium bromide; 4-Methoxybenzylmagnesium chloride; 4-Methylbenzylmagnesium chloride; m-Methylbenzylmagnesium chloride; 2-Methylbenzylmagnesium chloride; 3-Chlorobenzylmagnesium chloride; 2-Chlorobenzylmagnesium chloride; m-Methoxybenzylmagnesium chloride; Benzylmagnesium chloride; (Phenylethynyl)magnesium bromide; 4-Fluorobenzylmagnesium chloride; Benzylmagnesium bromide; 4-Chlorobenzylmagnesium chloride; and 2-Chloro-6-fluorobenzylmagnesium chloride to form a magnesium salt;

reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 72$^{nd}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of 2,5-Dimethylbenzylmagnesium chloride; 2,4-Dimethylbenzylmagnesium chloride; (2-Phenylethyl)magnesium chloride; 4-Methoxybenzylmagnesium chloride; 4-Methylbenzylmagnesium chloride; m-Methylbenzylmagnesium chloride; 2-Methylbenzylmagnesium chloride; m-Methoxybenzylmagnesium chloride; Benzylmagnesium chloride; and Benzylmagnesium bromide to form a magnesium salt; reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 73$^{rd}$ embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with Benzylmagnesium chloride to form a magnesium salt;

reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 74th embodiment, the invention is represented by the process to manufacture a compound of Formula IX, X, XI or XII or salts thereof

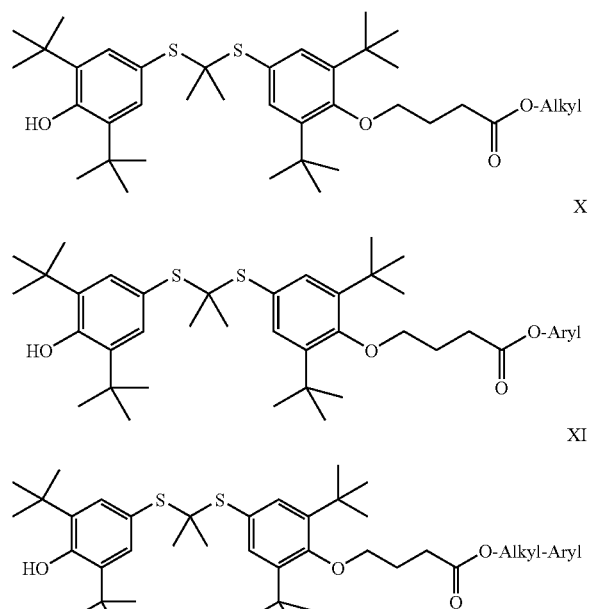

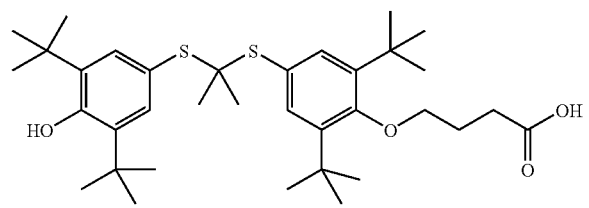

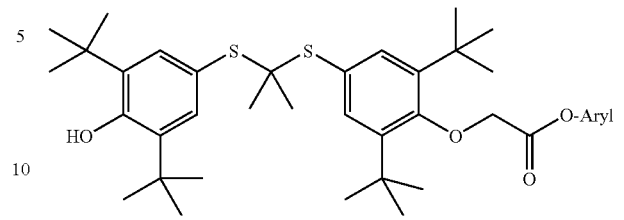

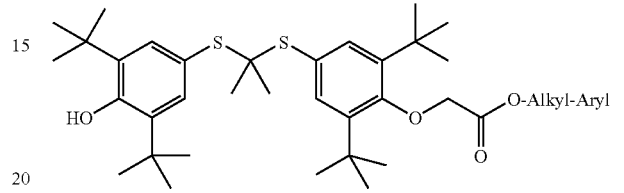

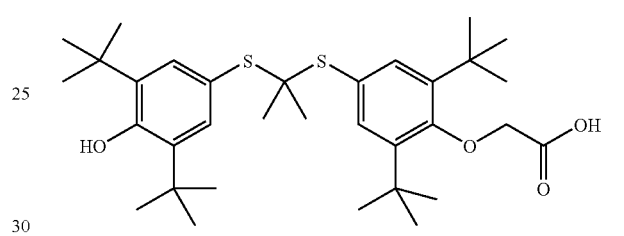

comprising:

reacting a solution of a compound of Formula IV with Benzylmagnesium chloride to form a magnesium salt;

reacting said magnesium salt with a compound selected form the group consisting of alkyl 4-halobutyrate, aryl 4-halobutyrate, aralkyl 4-halobutyrate and butyrolactone; separating and isolating said compound of Formula IX, X, XI or XII or salts thereof.

In a 75th embodiment, the invention is represented by the process to manufacture a compound of Formula XIII, XIV, XV or XVI or salts thereof

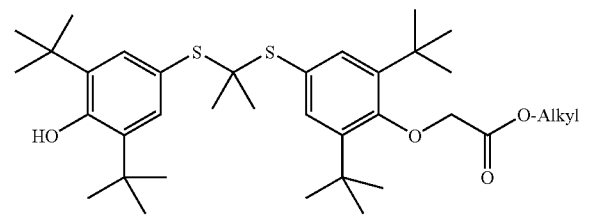

comprising:

reacting a compound of Formula IV with Benzylmagnesium chloride to form a magnesium salt;

reacting said magnesium salt with alkyl haloacetate, aryl haloacetate, aralkyl haloacetate, and alkali metal haloacetate;

separating and isolating said compound of Formula XIII, XIV, XV or XVI or salts thereof.

In a 76th embodiment, the invention is represented by the process to manufacture a compound of Formula XVII or salts thereof

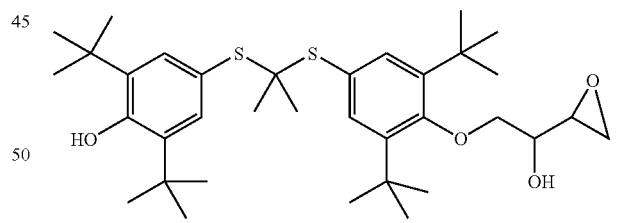

comprising:

reacting a compound of Formula IV with Benzylmagnesium chloride to form a magnesium salt;

reacting said magnesium salt with diepoxybutane;

separating and isolating said compound of Formula XVII or salts thereof.

In a 77th embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from alkylmagnesium alkyl or arylmagnesium aryl to form a magnesium salt, wherein said alkylmagnesium alkyl and arylmagnesium aryl may optionally be substituted by one or more selected from the group consisting of protected hydroxy, alkyl, alkenyl, protected acyl, nitro, protected amino, halo and protected carboxy;

reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In a 78th embodiment, the invention is represented by the process to manufacture a compound of Formula III or salts thereof wherein:

X is hydrogen;

Y is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano;

separating and isolating said compound of Formula III or salts thereof.

In an 79th embodiment, the invention is represented by the process to manufacture a compound of Formula IX, X, XI or XII or salts thereof

IX

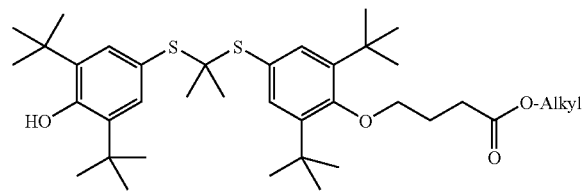

-continued

X

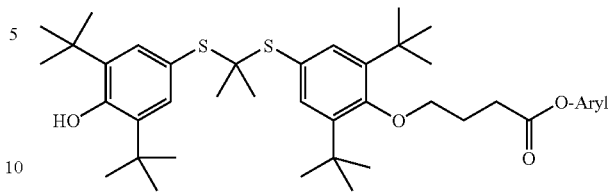

XI

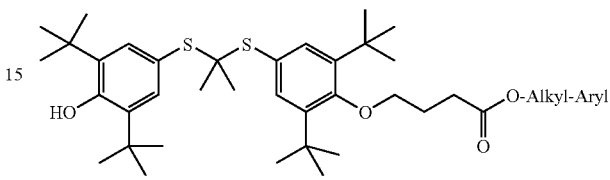

XII

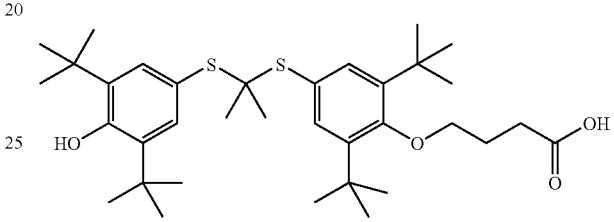

comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with a compound from the group consisting of alkyl 4-halobutyrate, aryl 4-halobutyrate, aralkyl 4-halobutyrate, and butyrolactone; separating and isolating said compound of Formula IX, X, XI or XII or salts thereof.

In an 80st embodiment, the invention is represented by the process to manufacture a compound of Formula XIII, XIV, XV or XVI or salts thereof

XIII

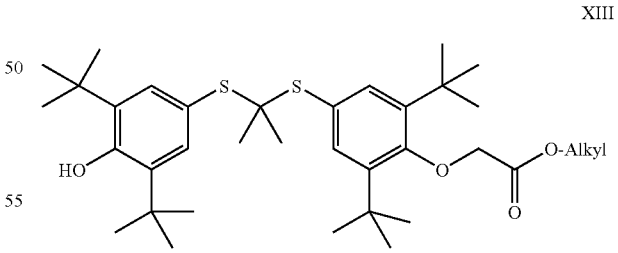

XIV

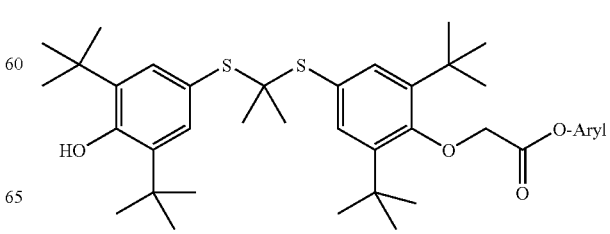

-continued

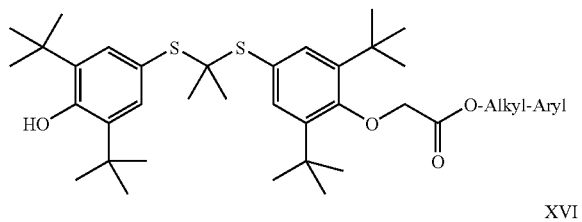
XV

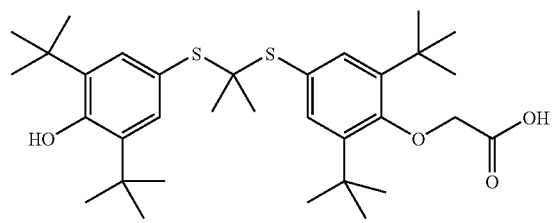
XVI comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with alkyl haloacetate, aryl haloacetate, aralkyl haloacetate, and alkali metal haloacetate;

separating and isolating said compound of Formula XIII, XIV, XV or XVI or salts thereof.

In an $81^{nd}$ embodiment, the invention is represented by the process to manufacture a compound of Formula XVII or salts thereof

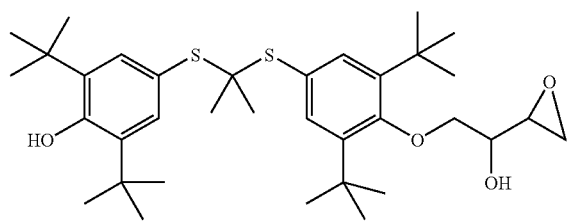
XVII comprising:

reacting a compound of Formula IV with a Grignard Reagent selected from the group consisting of n-Butyl-sec-butylmagnesium; Dimethylmagnesium; Di-n-Butylmagnesium; Diethylmagnesium; and Diphenylmagnesium to form a magnesium salt;

reacting said magnesium salt with diepoxybutane;

separating and isolating said compound of Formula XVII or salts thereof.

In an $82^{nd}$ embodiment, the invention is represented by the process to manufacture a compound of Formula XII or salts thereof

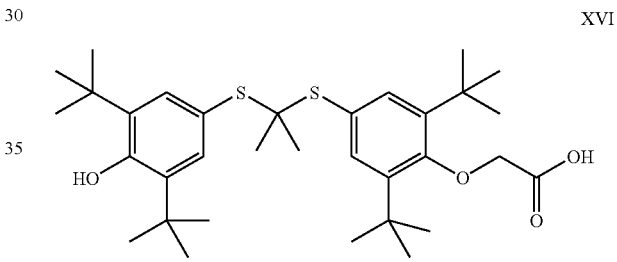
XII comprising:

reacting a compound of Formula IV with a Grignard Reagent to form a magnesium salt;

reacting said magnesium salt with alkyl haloacetate, aryl haloacetate or aralkyl haloacetate to form the compound of IX, X or XI;

hydrolyzing said compound of IX, X or XI;

separating and isolating said compound of Formula XII or salts thereof.

In an $83^{rd}$ embodiment, the invention is represented by the process to manufacture a compound of Formula XVI or salts thereof

XVI comprising:

reacting a compound of Formula IV with a Grignard Reagent to form a magnesium salt;

reacting said magnesium salt with alkyl haloacetate, aryl haloacetate, or aralkyl haloacetate to form the compound of XIII, XIV or XV;

hydrolyzing said compound of XIII, XIV or XV;

separating and isolating said compound of Formula XVI or salts thereof.

DEFINITIONS

The terms "alkyl" or "alk", alone or in combination, unless otherwise specified, refers to a saturated straight, branched or cyclic primary, secondary, or tertiary hydrocarbon from 1 to 18 carbon atoms and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl, trifluoromethyl and perfluoroalkyl. The term includes both substituted and unsubstituted alkyl groups. The alkyl group can be substituted with any moiety that does not adversely affect the properties of the active compound, for example, but not limited to hydroxyl, halo (including independently F, Cl, Br, and I), perfluoro alkyl including trifluoromethyl, amino, alkylamino, arylamino, alkoxy, aryloxy, nitro, cyano, acyl, amido, carboxamido, carboxylate, thiol, alkylthio, azido, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. In one embodiment, the alkyl can be, for example, $CF_3$, $CH_2CF_3$, $CCl_3$, or cyclopropyl.

In the text, whenever the term C (alkyl range) is used, the term independently includes each member of that class as if specifically and separately set out. As a non-limiting example, the term "$C_{1-10}$" independently represents each species that falls within the scope, including, but not limited to, methyl, ethyl, propyl, isopropyl, butyl, sec-butyl, iso-butyl, tert-butyl, pentyl, iso-pentyl, neo-pentyl, cyclopentyl, cyclopentyl, hexyl, 1-methylpentyl, 2-methylpentyl, 3-methylpentyl, 4-methylpentyl, 1-ethylbutyl, 2-ethylbutyl, 3-ethylbutyl, 4-ethyl butyl, cyclohexyl, heptyl, 1-methylhexyl, 2-methylhexyl, 3-methylhexyl, 4-methylhexyl, 5-methylhexyl, 6-methylhexyl, 1-ethylpentyl, 2-ethylpentyl, 3-ethylpentyl, 4-ethylpentyl, 5-ethylpentyl, 1-propylbutyl, 2-propylbutyl, 3-propylbutyl, 4-propylbutyl, cycloheptyl, octyl, 1-methylheptyl, 2-methylheptyl, 3-methylheptyl, 4-methylheptyl, 5-methylheptyl, 6-methylheptyl, 7-methylheptyl, 1-ethylhexyl, 2-ethylhexyl, 3-ethylhexyl, 4-ethylhexyl, 5-ethylhexyl, 6-ethylhexyl, 1-propylpentyl, 2-propylpentyl, 3-propylpentyl, 4-propylpentyl, 5-propylpentyl, cyclooctyl, nonyl, cyclononyl, decyl, or cyclodecyl. $C_{1-6}$, $C_{1-8}$, $C_{2-8}$, $C_{3-8}$, $C_{1-10}$ and $C_{1-18}$ likewise can independently include any of its member groups, as if each were independently named herein.

The term "alkenyl", alone or in combination, unless otherwise specified refers to a straight, branched or cyclic hydrocarbon having from 2 to 10 carbon atoms and containing one or more double carbon-carbon bonds. Examples of such radicals are methylene, ethylene, methylethylene, and isopropylidene. Included within the scope of this term are 1,2-ethane-diyl, 1,1-ethane-diyl, 1,3-propane-diyl, 1,2-propane-diyl, 1,3-butane-diyl, 1,4-butane-diyl and the like. The alkylene group or other divalent moiety disclosed herein can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "alkynyl" refers to an unsaturated, acyclic hydrocarbon radical, linear or branched, in so much as it contains one or more triple bonds, including such radicals containing about 2 to 10 carbon atoms or having from 2 to 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "aryl" or "ar", alone or in combination, means a carbocyclic aromatic system containing one, two or three rings wherein such rings may be attached together in a pendent manner or may be fused. The term "aryl" also includes an "aryl" optionally substituted with one or more of the moieties selected from the group consisting of alkyl, alkenyl, and alkynyl, alkoxy, aryloxy, halo, and amino.

The term "acyl", alone or in combination, refers to a group of the formula C(O)R', wherein R' is hydrogen, alkyl, alkenyl, alkynyl, aryl, or aralkyl group. Examples of "acyl" are formyl, acetyl, benzoyl, trifluoroacetyl, phthaloyl, malonyl, nicotinyl, and the like.

The term "amino", alone or in combination, refers to the radical —$NH_2$ or —NH—, or

The term "alkoxy", alone or in combination, refers to an alkyl group as defined herein bonded through an oxygen linkage. Examples of alkoxys include methoxy, ethoxy, propoxy, butoxy, isopropoxy and tert-butoxy alkyls.

The term "aryloxy", alone or in combination, refers to an aryl group as defined herein bonded through an oxygen linkage.

The term "alkthio", alone or in combination, refers to an alkyl group as defined herein bonded through a sulfur linkage.

The term "carboxy", refers to the radical

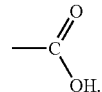

The terms "halo" and "halogen" and "halide", alone or in combination, refer to chloro, bromo, iodo and fluoro.

The term "substituted", means that one or more hydrogen on the designated atom or substituent is replaced provided that the designated atom's normal valency is not exceeded, and the that the substitution results in a stable compound. Typical substitutions include, hydroxy, alkyl, alkenyl, acyl, nitro, amino, halo, carboxy, cyano and protecting groups as defined herein. Such substitutions can be further substituted.

The term "polar or charged functionality" refers to a polar or charged group attached in place of one or more hydrogen atoms. Non limiting examples include carboxy, hydroxy, amino, epoxide, etc.

The terms "heteroaryl", alone or in combination, refer to an aryl as defined herein containing at least one heteroatom selected from sulfur, oxygen, nitrogen or phosphorus. The heteroaryl may optionally be substituted as that term is used herein and/or substituted with a protecting group as that term is used herein. In addition, adjacent groups on the heteroaryl may combine to form a 5- to 7-membered carbocyclic, aryl, heteroaryl, which in turn may be substituted as above. Non-limiting examples of heteroaryls are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl, aziridinyl, furyl, furanyl, pyridyl, pyridinyl, pyridazinyl, pyrimidinyl, benzoxazolyl, 1,2,4-oxadiazolyl, 1,3,4-oxadiazolyl, 1,3,4-thiadiazole, indazolyl, triazinayl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, 1,2,4-oxadiazolyl, 1,3,4-oxadiazolyl, pyrrolyl, quinazolinyl, quinoxalinyl, benzoxazolyl, quinolinyl, isoquinolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, triazolopyridinyl or pteridinyl, wherein said heteroaryl can be optionally substituted.

The terms "protecting group" or "protected" refers to a substituent that protects various sensitive or reactive groups present, so as to prevent said groups from interfering with a reaction. Such protection may be carried out in a well-known manner as taught by Greene, et al., *Protective Groups in Organic Synthesis*, John Wiley and Sons, Second Edition, 1991 or of the like. The protecting group may be removed after the reaction in any manner known by those skilled in the art. Non-limiting examples of protecting groups include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl. For example, a protected carboxy could be selected from one of the following:

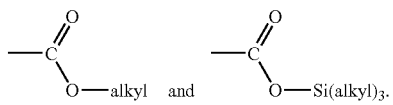

The term "carboxylic acid anhydride", alone or in combination refers to compounds having the formulas acyl-OC(O)$R^\alpha$, acyl-OC(O)O$R^\alpha$, acyl-OC(O)S$R^\alpha$, or acyl-OC(O)N$R^\alpha R^\beta$ wherein $R^\alpha$ is selected from the group consisting of alkyl, alkenyl, alkynyl, aryl, and aralkyl and $R^\beta$ is selected from the group consisting of alkyl, alkenyl, alkynyl, aryl, alkaryl, aralkyl and a protecting group (as that term is defined herein). The term "carboxylic anhydride" includes "cyclic carboxylic acid anhydride", which refers to compounds having the formula

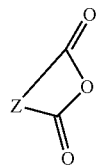

wherein Z is selected from alkyl, alkenyl, alkynyl, aryl, aralkyl and —(CH$_2$)NR$^\beta$. All "carboxylic acid anhydrides" may optionally be substituted as defined herein.

The term "activated carboxylic acid ester" refers to compounds having the formula C(O)SR" and C(O)OR", wherein R" is a substituted or unsubstituted aryl or an unsubstituted or substituted alkyl.

The term "Grignard Reagent" generally means an organic magnesium halide (as defined by The Columbia Encyclopedia, Sixth Edition, 2001, herein incorporated by reference) or a bis-organic magnesium compound represented by the formulas R$^\gamma$MgX and R$^\gamma$MgR$^\delta$ respectively, wherein R$^\gamma$ and R$^\delta$ are independently selected from the group consisting of a primary, secondary, or tertiary alkyl; alkenyl; alkynyl; aralkyl; heteroaryl; and aryl, all of which can be substituted as that term is defined herein, and X is represented by a halide.

The term "sulfonyl" refers to the radical

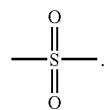

The term "alksulfonyl" refers to the radical

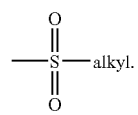

The term "epoxide" refers to

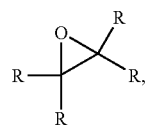

wherein all R groups are independently selected from hydrogen, alkyl, aryl and arylalkyl wherein said alkyl, aryl and arylalkyl may optionally be substituted with a polar functionality.

The terms "esters of probucol" and "esters of probucol derivatives" are defined as probucol or probucol derivatives (as the case may be) wherein one or both of the phenol moieties are acylated. The terms "monoesters of probucol" and "monoesters of probucol derivatives" are defined as probucol or probucol derivatives (as the case may be) wherein one of the phenol moieties are acylated.

The terms "ethers of probucol" and "ethers of probucol derivatives" are defined as probucol or probucol derivatives (as the case may be) wherein one or both of the phenol moieties are alkylated. The terms "monoethers of probucol" and "monoethers of probucol derivatives" are defined as probucol or probucol derivatives (as the case may be) wherein one of the phenol moieties are alkylated.

The term "probucol derivative" refers to the compound

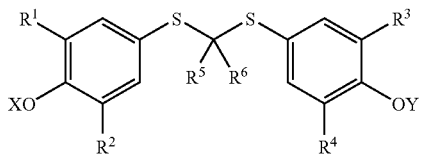

wherein at least one $R^1$, $R^2$, $R^3$, and $R^4$ is other than t-butyl and/or one or both of $R^5$ and $R^6$ are other than methyl and/or one or both of X and Y are other than hydrogen.

EXAMPLES

The following examples are provided to illustrate the present invention and are not intended to limit the scope thereof. Those skilled in the art will readily understand that known variations of the conditions and processes of the following preparative procedures can be used to manufacture the desired compounds. The materials required for the embodiments and the examples are known in the literature, readily commercially available, or can be made by known methods from known starting materials by those skilled in the art.

Example 1

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium chloride (0.51 mL, 2.0 M in THF) in 1 portion. The reaction was brought to room temperature and then succinic anhydride (0.25 g, 2.5 mmol) was added in 1 portion. After aging for 45 min, the reaction was slowly quenched with 1 N HCl and diluted with EtOAc. The biphasic reaction was then cooled to room temperature and the phases were separated. Analysis by HPLC of the organic layer indicated 60% probucol monosuccinate, 13% probucol disuccinate, and 27% probucol.

Example 2

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium bromide (1.0 mL, 1.0 M in THF) in 1 portion. The reaction was brought to room temperature and then succinic anhydride (0.25 g, 2.5 mmol) was added in 1 portion followed by anhydrous THF (0.5 mL). After aging for 1.5 h, the reaction was slowly quenched with 1 N HCl and diluted with EtOAc. The biphasic reaction was then cooled to room temperature and the phases were separated. Analysis by HPLC of the organic layer indicated 55% probucol monosuccinate, 27% probucol disuccinate, and 18% probucol.

Example 3

In a dry 25 mL 3-neck round bottom fitted with a reflux condenser, nitrogen inlet, thermocouple and stir bar was charged probucol (0.25 g, 0.48 mmol) and succinic anhydride (0.25 g, 2.5 mmol) followed by 2.5 mL anhydrous toluene. To the resulting solution was added isopropylmagnesium chloride (0.51 mL, 2.0 M in THF) over 2 min. After aging for 40 min, the reaction was slowly quenched with 1 N HCl and diluted with EtOAc. The biphasic reaction was then cooled to room temperature and the phases were separated. Analysis by HPLC of the organic layer indicated 53% probucol monosuccinate, 17% probucol disuccinate, and 30% probucol.

Example 4

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium chloride (0.51 mL, 2.0 M in THF) in 1 portion. The reaction temperature was brought to 5° C. and then succinic anhydride (0.25 g, 2.5 mmol) was added in 1 portion. After aging for 45 min, the reaction was slowly quenched with 1 N HCl and diluted with EtOAc. The biphasic reaction was then cooled to room temperature and the phases were separated. Analysis by HPLC of the organic layer indicated 46% probucol monosuccinate, 47% probucol disuccinate, and 7% probucol.

Example 5

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium chloride (0.51 mL, 2.0 M in THF) in 1 portion. The reaction was brought to room temperature and then succinic anhydride (125.0 mg, 1.25 mmol) was added as a solution in THF (1.5 mL) over 5 min. After aging for 40 min, analysis by HPLC of the reaction mixture indicated 55% probucol monosuccinate, 17% probucol disuccinate, and 28% probucol.

Example 6

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium chloride (0.51 mL, 2.0 M in THF) in 1 portion. The reaction temperature was brought to 40° C. and then succinic anhydride (125.0 mg, 1.25 mmol) was added as a solution in THF (1.5 mL) over 5 min. After aging for 20 min, the reaction was slowly quenched with 1 N HCl and diluted with EtOAc. The biphasic reaction was then cooled to room temperature and the phases were separated. Analysis by HPLC of the organic layer indicated 51% probucol monosuccinate, 32% probucol disuccinate, and 17% probucol.

Example 7

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium chloride (0.51 mL, 2.0 M in THF) in 1 portion. The reaction temperature was brought to 60° C. and then succinic anhydride (125.0 mg, 1.25 mmol) was added as a solution in THF (1.5 mL) over 5 min. After aging for 20 min, the reaction was slowly quenched with 1 N HCl and diluted with EtOAc. The biphasic reaction was then cooled to room temperature and the phases were separated. Analysis by HPLC of the organic layer indicated 45% probucol monosuccinate, 45% probucol disuccinate, and 10% probucol.

Example 8

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium chloride (0.51 mL, 2.0 M in THF) in 1 portion. The reaction was brought to room temperature and then succinic anhydride (75.0 mg, 0.75 mmol) was added as a solution in THF (1 mL) over 5 min. After aging for 45 min, the reaction was slowly quenched with 1 N HCl and diluted with EtOAc. The biphasic reaction was then cooled to room temperature and the phases were separated. Analysis by HPLC of the organic layer indicated 59% probucol monosuccinate, 20% probucol disuccinate, and 21% probucol.

Example 9

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium chloride (0.51 mL, 2.0 M in THF) in 1 portion. The reaction temperature was brought to 40° C. and then succinic anhydride (75.0 mg, 0.75 mmol) was added as a solution in THF (1 mL) over 5 min. After aging for 20 min, the reaction was slowly quenched with 1 N HCl and diluted with EtOAc. The biphasic reaction was then cooled to room temperature and the phases were separated. Analysis by HPLC of the organic layer indicated 59% probucol monosuccinate, 20% probucol disuccinate, and 21% probucol.

Example 10

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added isopropylmagnesium chloride (0.51 mL, 2.0 M in THF) in 1 portion. The reaction temperature was brought to 60° C. and then succinic anhydride (75.0 mg, 0.75 mmol) was added as a solution in THF (1 mL) over 5 min. After aging for 20 min, the reaction was slowly quenched with 1 N HCl and diluted with EtOAc. The biphasic reaction was then cooled to room temperature and the phases were separated. Analysis by HPLC of the organic layer indicated 59% probucol monosuccinate, 26% probucol disuccinate, and 15% probucol.

Example 11

In a dry 25 mL 3-neck round bottom fitted with a reflux condenser, nitrogen inlet, thermocouple and stir bar was charged probucol (0.25 g, 0.48 mmol) followed by 5 mL anhydrous toluene. To the resulting solution was added isopropylmagnesium chloride (0.51 mL, 2.0 M in THF) in 1 portion. The reaction was brought to room temperature and then succinic anhydride (75.0 mg, 0.75 mmol) was added as a solution in THF (1 mL) over 5 min. After aging for 45 min, analysis by HPLC of the reaction mixture indicated 54% probucol monosuccinate, 10% probucol disuccinate, and 34% probucol.

Example 12

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene and 0.5 mL anhydrous hexane. To the resulting solution was added isopropylmagnesium chloride (0.51 mL, 2.0 M in THF) in 1 portion. The reaction temperature was brought to room temperature and then succinic anhydride (75.0 mg, 0.75 mmol) was added over 5 min. After aging for 45 min, analysis by HPLC of the reaction mixture indicated 57% probucol monosuccinate, 16% probucol disuccinate, and 27% probucol.

Example 13

In a dry 25 mL 3-neck round bottom fitted with a reflux condenser, nitrogen inlet, thermocouple and stir bar was charged probucol (0.25 g, 0.48 mmol) followed by 5 mL anhydrous toluene. To the resulting solution was added cyclopentylmagnesium chloride (0.51 mL, 2.0 M in ethyl ether) in 1 portion. The reaction was brought to room temperature and then succinic anhydride (75.0 mg, 0.75 mmol) was added in 1 portion and aged overnight. Analysis by HPLC of the reaction mixture indicated 47% probucol monosuccinate, 14% probucol disuccinate, and 39% probucol.

Example 14

In a dry 25 mL 3-neck round bottom fitted with a reflux condenser, nitrogen inlet, thermocouple and stir bar was charged probucol (0.25 g, 0.48 mmol) followed by 5 mL anhydrous toluene. To the resulting solution was added cyclohexylmagnesium chloride (0.51 mL, 2.0 M in ethyl ether) in 1 portion. The reaction was brought to room temperature and then succinic anhydride (75.0 mg, 0.75 mmol) was added in 1 portion and aged overnight. Analysis by HPLC of the reaction mixture indicated 48% probucol monosuccinate, 14% probucol disuccinate, and 38% probucol.

Example 15

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene. To the resulting solution was added benzylmagnesium chloride (1.02 mL, 1.0 M in ethyl ether) in 1 portion. The reaction temperature was brought to 40° C. and then succinic anhydride (75.0 mg, 0.75 mmol) was added in 1 portion and aged overnight. Analysis by HPLC of the reaction mixture indicated 50% probucol monosuccinate, 14% probucol disuccinate, and 36% probucol.

Example 16

In a dry 25 mL 3-neck round bottom fitted with a reflux condenser, nitrogen inlet, thermocouple and stir bar was charged probucol (0.25 g, 0.48 mmol) followed by 2.5 mL anhydrous THF. To the resulting solution was added benzylmagnesium chloride (0.51 mL, 2.0 M in THF) in 1 portion. The reaction temperature was brought to 60° C. and then succinic anhydride (75.0 mg, 0.75 mmol) was added in 1 portion. After aging for 30 min, the reaction was slowly quenched with 1 N HCl and diluted with EtOAc. The biphasic reaction was then cooled to room temperature and the phases were separated. Analysis by HPLC of the organic layer indicated 57% probucol monosuccinate, 17% probucol disuccinate, and 28% probucol.

Example 17

In a dry 25 mL 3-neck round bottom fitted with a reflux condenser, nitrogen inlet, thermocouple and stir bar was charged probucol (0.25 g, 0.48 mmol) followed by 2.5 mL anhydrous THF. To the resulting solution was added benzylmagnesium chloride (0.51 mL, 2.0 M in THF) in 1 portion. The reaction temperature was brought to 40° C. and then succinic anhydride (75.0 mg, 0.75 mmol) was added in 1 portion. After aging for 30 min, the reaction was slowly quenched with 1 N HCl and diluted with EtOAc. The biphasic reaction was then cooled to room temperature and the phases were separated. Analysis by HPLC of the organic layer indicated 53% probucol monosuccinate, 11% probucol disuccinate, and 36% probucol.

Example 18

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene and 2.0 mL anhydrous tetrahydrofuran (THF). To the resulting solution was added benzylmagnesium chloride (0.51 mL, 2.0 M in THF) in 1 portion. The reaction temperature was brought to 40° C. and then succinic anhydride (75.0 mg, 0.75 mmol) was added in 1 portion. After aging for 30 min, the reaction was slowly quenched with 1 N HCl and diluted with EtOAc. The biphasic reaction was then cooled to room temperature and the phases were separated. Analysis by HPLC of the organic layer indicated 55% probucol monosuccinate, 24% probucol disuccinate, and 21% probucol.

Example 19

In a dry 25 mL 3-neck round bottom fitted with a reflux condenser, nitrogen inlet, thermocouple and stir bar was charged probucol (0.25 g, 0.48 mmol) followed by 2.5 mL anhydrous toluene and 2.0 mL anhydrous THF. To the resulting solution was added benzylmagnesium chloride (0.51 mL, 2.0 M in THF) in 1 portion. The reaction temperature was brought to room temperature and then succinic anhydride (75.0 mg, 0.75 mmol) was added in 1 portion. After aging for 30 min, the reaction was slowly quenched with 1 N HCl and diluted with EtOAc. The biphasic reaction was then cooled to room temperature and the phases were separated. Analysis by HPLC of the organic layer indicated 50% probucol monosuccinate, 9% probucol disuccinate, and 41% probucol.

Example 20

In a dry 25 mL 3-neck round bottom fitted with a reflux condenser, nitrogen inlet, thermocouple and stir bar was charged probucol (0.25 g, 0.48 mmol) followed by 4.5 mL anhydrous THF. To the resulting solution was added benzylmagnesium chloride (0.51 mL, 2.0 M in THF) in 1 portion. The reaction temperature was brought to 40° C. and then succinic anhydride (75.0 mg, 0.75 mmol) was added in 1 portion. After aging for 30 min, analysis by HPLC of the reaction mixture indicated 45% probucol monosuccinate, 7% probucol disuccinate, and 48% probucol.

Example 21

In a dry 25 mL 3-neck round bottom fitted with a reflux condenser, nitrogen inlet, thermocouple and stir bar was charged probucol (0.25 g, 0.48 mmol) followed by 2.5 mL anhydrous THF. To the resulting solution was added benzylmagnesium chloride (0.51 mL, 2.0 M in THF) in 1 portion. The reaction temperature was brought to 50° C. and then succinic anhydride (55.0 mg, 0.55 mmol) was added in 1 portion. After aging for 30 min, analysis by HPLC of the reaction mixture indicated 52% probucol monosuccinate, 7% probucol disuccinate, and 41% probucol.

Example 22

In a dry 25 mL 3-neck round bottom fitted with a reflux condenser, nitrogen inlet, thermocouple and stir bar was charged probucol (0.25 g, 0.48 mmol) followed by 2.5 mL anhydrous THF. To the resulting solution was added benzylmagnesium chloride (0.51 mL, 2.0 M in THF) in 1 portion. The reaction temperature was brought to 40° C. and then succinic anhydride (55.0 mg, 0.55 mmol) was added in 1 portion. After aging for 30 min, analysis by HPLC of the reaction mixture indicated 51% probucol monosuccinate, 7% probucol disuccinate, and 42% probucol.

Example 23

In a dry 25 mL 3-neck round bottom fitted with a reflux condenser, nitrogen inlet, thermocouple and stir bar was charged probucol (0.25 g, 0.48 mmol) followed by 1 mL anhydrous THF. To the resulting solution was added benzylmagnesium chloride (0.51 mL, 2.0 M in THF) in 1 portion. The reaction temperature was brought to 40° C. and then succinic anhydride (55.0 mg, 0.55 mmol) was added in 1 portion. After aging for 45 min, analysis by HPLC of the reaction mixture indicated 57% probucol monosuccinate, 9% probucol disuccinate, and 34% probucol.

Example 24

In a dry 25 mL 3-neck round bottom fitted with a reflux condenser, nitrogen inlet, thermocouple and stir bar was charged probucol (0.25 g, 0.48 mmol) followed by 1 mL anhydrous anisole. To the resulting solution was added benzylmagnesium chloride (0.51 mL, 2.0 M in THF) in 1 portion. The reaction temperature was brought to 40° C. and then succinic anhydride (55.0 mg, 0.55 mmol) was added in 1 portion. After aging for 45 min, analysis by HPLC of the reaction mixture indicated 58% probucol monosuccinate, 10% probucol disuccinate, and 32% probucol.

Example 25

In a dry 25 mL 3-neck round bottom fitted with a reflux condenser, nitrogen inlet, thermocouple and stir bar was charged probucol (0.25 g, 0.48 mmol) followed by 0.5 mL anhydrous anisole. To the resulting solution was added 2-methoxyphenylmagnesium bromide (1.02 mL, 1.0 M in THF) in 1 portion. The reaction temperature was brought to 40° C. and then succinic anhydride (55.0 mg, 0.55 mmol) was added in 1 portion. After aging for 45 min, analysis by HPLC of the reaction mixture indicated 42% probucol monosuccinate, 6% probucol disuccinate, and 52% probucol.

Example 26

In a dry 25 mL 3-neck round bottom fitted with a reflux condenser, nitrogen inlet, thermocouple and stir bar was charged probucol (0.25 g, 0.48 mmol) followed by 0.5 mL anhydrous anisole. To the resulting solution was added 3-methoxyphenylmagnesium bromide (1.02 mL, 1.0 M in THF) in 1 portion. The reaction temperature was brought to 40° C. and then succinic anhydride (55.0 mg, 0.55 mmol) was added in 1 portion. After aging for 45 min, analysis by HPLC of the reaction mixture indicated 45% probucol monosuccinate, 5% probucol disuccinate, and 50% probucol.

Example 27

In a dry 25 mL 3-neck round bottom fitted with a reflux condenser, nitrogen inlet, thermocouple and stir bar was charged probucol (0.25 g, 0.48 mmol) followed by 1 mL anhydrous toluene. To the resulting solution was added benzylmagnesium chloride (0.51 mL, 2.0 M in THF) in 1 portion. The reaction temperature was brought to 40° C. and then succinic anhydride (55.0 mg, 0.55 mmol) was added in 1 portion. After slowly quenching the reaction with 1 N HCl and diluting with EtOAc, the biphasic reaction was cooled to room temperature and the phases were separated. Analysis by HPLC of the organic layer indicated 50% probucol monosuccinate, 8% probucol disuccinate, and 42% probucol.

Example 28

In a dry 25 mL 3-neck round bottom fitted with a reflux condenser, nitrogen inlet, thermocouple and stir bar was charged probucol (0.25 g, 0.48 mmol) followed by 1 mL anhydrous THF. To the resulting solution was added octylmagnesium chloride (0.51 mL, 2.0 M in THF) in 1 portion. The reaction temperature was brought to 40° C. and then succinic anhydride (55.0 mg, 0.55 mmol) was added in 1 portion. After aging for 45 min, analysis by HPLC of the reaction mixture indicated 53% probucol monosuccinate, 12% probucol disuccinate, and 35% probucol.

Example 29

In a dry 25 mL 3-neck round bottom fitted with a reflux condenser, nitrogen inlet, thermocouple and stir bar was charged probucol (0.25 g, 0.48 mmol) followed by 0.25 mL anhydrous THF. To the resulting solution was added benzylmagnesium chloride (0.51 mL, 2.0 M in THF) in 1 portion. The reaction temperature was brought to 40° C. and then succinic anhydride (55.0 mg, 0.55 mmol) was added in 1 portion. After aging for 45 min, analysis by HPLC of the reaction mixture indicated 50% probucol monosuccinate, 7% probucol disuccinate, and 43% probucol.

Example 30

In a dry 50 mL 3-neck round bottom fitted with a reflux condenser, nitrogen inlet, thermocouple and stir bar was charged probucol (5.0 g, 9.67 mmol) followed by 20 mL anhydrous tetrahydrofuran (THF). To the resulting solution was slowly added benzylmagnesium chloride (10.08 mL, 2.0 M in THF) over 2 min. Once addition was complete the reaction temperature was brought to 40° C. and then succinic anhydride (1.1 g, 10.99 mmol) was added in 1 portion. After aging for 15 min, analysis by HPLC of the reaction mixture indicated 58% probucol monosuccinate, 10% probucol disuccinate, and 32% probucol.

Example 31

In a dry 50 mL 3-neck round bottom fitted with a reflux condenser, nitrogen inlet, thermocouple and stir bar was charged probucol (5.0 g, 9.67 mmol) followed by 20 mL anhydrous tetrahydrofuran (THF). To the resulting solution was slowly added octylmagnesium chloride (10.06 mL, 2.0 M in THF) over 2 min. Once addition was complete the reaction temperature was brought to 40° C. and then succinic anhydride (1.1 g, 10.99 mmol) was added in 1 portion. After slowly quenching the reaction with 1 N HCl and diluting with EtOAc, the biphasic reaction was cooled to room temperature and the phases were separated. Analysis by HPLC of the reaction mixture indicated 53% probucol monosuccinate, 8% probucol disuccinate, and 39% probucol.

Example 32

In a dry 50 mL 3-neck round bottom fitted with a reflux condenser, nitrogen inlet, thermocouple and stir bar was charged probucol (5.0 g, 9.67 mmol) followed by 20 mL anhydrous THF. To the resulting solution was slowly added benzylmagnesium chloride (9.91 mL, 2.0 M in THF) at such a rate to maintain the internal reaction temperature between 40-50° C. Once addition was complete the reaction temperature was brought to 40° C. and then succinic anhydride (1.03 g, 10.29 mmol) was added in 1 portion. After aging for 15 min, analysis by HPLC of the reaction mixture indicated 56% probucol monosuccinate, 9% probucol disuccinate, and 35% probucol.

Example 33

In a dry 50 mL 3-neck round bottom fitted with a reflux condenser, nitrogen inlet, thermocouple and stir bar was charged probucol (5.0 g, 9.67 mmol) followed by 10 mL anhydrous THF. To the resulting solution was slowly added benzylmagnesium chloride (9.88 mL, 2.0 M in THF) at such a rate to maintain the internal reaction temperature between 40-50° C. Once addition was complete the reaction temperature was brought to 40° C. and then succinic anhydride (0.965 g, 9.64 mmol) was added as a THF (10 mL) solution over 45 min. After aging for 45 min, analysis by HPLC of the reaction mixture indicated 58% probucol monosuccinate, 8% probucol disuccinate, and 34% probucol.

Example 34

In a dry 50 mL 3-neck round bottom fitted with a reflux condenser, nitrogen inlet, thermocouple and stir bar was charged probucol (5.0 g, 9.67 mmol) followed by 20 mL anhydrous THF. To the resulting solution was slowly added benzylmagnesium chloride (10.8 mL, 2.0 M in THF) at such a rate to maintain the internal reaction temperature between 40-50° C. Once addition was complete the reaction temperature was brought to 40° C. and then succinic anhydride (1.03 g, 10.29 mmol) was added in 1 portion. After aging 45 min, analysis by HPLC of the reaction mixture indicated 52% probucol monosuccinate, 6% probucol disuccinate, and 42% probucol.

Example 35

In a dry 50 mL 3-neck round bottom fitted with a reflux condenser, nitrogen inlet, thermocouple and stir bar was charged probucol (5.0 g, 9.67 mmol) followed by 20 mL anhydrous THF. To the resulting solution was slowly added benzylmagnesium chloride (8.9 mL, 2.0 M in THF) at such a rate to maintain the internal reaction temperature between 40-50° C. Once addition was complete the reaction temperature was brought to 40° C. and then succinic anhydride (1.03 g, 10.29 mmol) was added in 1 portion. After aging 45 min, analysis by HPLC of the reaction mixture indicated 56% probucol monosuccinate, 11% probucol disuccinate, and 33% probucol.

Example 36

In a dry 50 mL 3-neck round bottom fitted with a reflux condenser, nitrogen inlet, thermocouple and stir bar was charged probucol (5.0 g, 9.67 mmol) followed by 20 mL anhydrous THF. To the resulting solution was slowly added benzylmagnesium chloride (8.2 mL, 2.0 M in THF) at such a rate to maintain the internal reaction temperature between 40-50° C. Once addition was complete the reaction temperature was brought to 40° C. and then succinic anhydride (1.03 g, 10.29 mmol) was added in 1 portion. After aging 40 min, analysis by HPLC of the reaction mixture indicated 52% probucol monosuccinate, 11% probucol disuccinate, and 37% probucol.

Example 37

In a dry 50 mL 3-neck round bottom fitted with a reflux condenser, nitrogen inlet, thermocouple and stir bar was charged probucol (5.0 g, 9.67 mmol) followed by 20 mL anhydrous THF. To the resulting solution was slowly added benzylmagnesium chloride (7.5 mL, 2.0 M in THF) at such a rate to maintain the internal reaction temperature between 40-50° C. Once addition was complete the reaction temperature was brought to 40° C. and then succinic anhydride (1.03 g, 10.29 mmol) was added in 1 portion. After aging 40 min, analysis by HPLC of the reaction mixture indicated 48% probucol monosuccinate, 10% probucol disuccinate, and 42% probucol.

Example 38

In a dry 50 mL 3-neck round bottom fitted with a reflux condenser, nitrogen inlet, thermocouple and stir bar was charged probucol (5.0 g, 9.67 mmol) followed by 10 mL anhydrous THF. To the resulting solution was slowly added benzylmagnesium chloride (9.86 mL, 2.0 M in THF) at such a rate to maintain the internal reaction temperature between 40-50° C. Once addition was complete the reaction temperature was brought to 40° C. and then succinic anhydride (1.03 g, 10.28 mmol) in THF (10.2 mL) was added over 30 min. After slowly quenching the reaction with 4 N HCl, the biphasic reaction was cooled to room temperature and the phases were separated. Analysis by HPLC of the organic layer at this point indicated 64% probucol monosuccinate, 13% probucol disuccinate, and 23% probucol.

Example 39

In a dry 50 mL 3-neck round bottom fitted with a reflux condenser, nitrogen inlet, thermocouple and stir bar was charged probucol (5.0 g, 9.67 mmol) followed by 10 mL anhydrous tetrahydrofuran (THF). To the resulting solution was slowly added benzylmagnesium chloride (9.86 mL, 2.0 M in THF) at such a rate to maintain the internal reaction temperature between 40-50° C. Once addition was complete the reaction temperature was brought to 40° C. and then succinic anhydride (1.03 g, 10.28 mmol) in THF (10.2 mL) was added over 30 min. Analysis by HPLC of the reaction mixture indicated 64% probucol monosuccinate, 13% probucol disuccinate, and 23% probucol. After slowly quenching the reaction with 4 N HCl, the biphasic reaction was cooled to room temperature and the phases were separated. The organic cut was diluted with THF and water and then the phases were separated again.

After washing the THF cut with 5 N NaOH, the THF solution was azeotropically dried under reduced pressure at 45° C. with the addition of dry THF. Following a solvent switch to heptane, the resulting slurry was cooled to 0° C. with stirring and vacuum filtered. The residue is washed with cold heptane and to the wet cake is added tert-butylmethyl ether (MTBE) with stirring. The resulting slurry was filtered and the residue washed with fresh MTBE. The MTBE filtrates were then combined and washed sequentially with 1 N HCl and water. The organic cut was then solvent switched to heptane at 70° C. under reduced pressure. The heptane solution was cooled to 5° C. over 45 min and the resulting slurry was filtered, washed with cold heptane and dried to yield 3.42 g MSP (57.3% yield, 97 LCAP) as a white solid, m.p. 139-142° C. $^1$H-NMR (300 MHz, CDCl$_3$): 7.62 (s, 2H), 7.45 (s, 2H), 5.37 (s, 1H), 3.00 (t, 2H, J=6.8 Hz), 2.78 (t, 2H, J=6.8 Hz), 1.46 (s, 6H), 1.44 (s, 18H), 1.34 (s, 18H).

Example 40

In a dry 10 mL round bottom fitted with nitrogen inlet, thermocouple and stir bar was charged probucol (1.0 g, 1.93 mmol) followed by 4 mL anhydrous THF. To the resulting solution was slowly added n-butyl lithium (1.58 mL, 2.5 M in hexanes) at such a rate to maintain the internal reaction temperature between 40-52° C. Once addition was complete additional THF (2 mL) was added and the reaction temperature was brought to 40° C. Solid succinic anhydride (0.20 g, 2.00 mmol) was added to the resulting solution in 1 portion. After aging for 15 min, analysis by HPLC of the reaction mixture indicated 15% probucol monosuccinate, 4% probucol disuccinate, and 81% probucol.

Example 41

In a dry 10 mL round bottom fitted with nitrogen inlet, thermocouple and stir bar was charged probucol (1.0 g, 1.93 mmol) followed by 4 mL anhydrous THF. To the resulting solution was slowly added hexyl lithium (1.70 mL, 2.3 M in hexanes) at such a rate to maintain the internal reaction temperature between 40-50° C. Once addition was complete additional THF (2 mL) was added and the reaction temperature was brought to 40° C. Solid succinic anhydride (0.20 g, 2.00 mmol) was added to the resulting solution in 1 portion. After aging for 15 min, analysis by HPLC of the reaction mixture indicated 20% probucol monosuccinate, 5% probucol disuccinate, and 75% probucol.

Example 42

In a dry 10 mL round bottom fitted with nitrogen inlet, thermocouple and stir bar was charged probucol (1.0 g, 1.93 mmol) followed by 4 mL anhydrous THF. To the resulting solution was slowly added hexyl lithium (1.70 mL, 2.3 M in hexanes) at such a rate to maintain the internal reaction temperature between 40-50° C. Once addition was complete DMF (2 mL) was added and the reaction temperature was brought to 40° C. Solid succinic anhydride (0.20 g, 2.00 mmol) was added to the resulting solution in 1 portion. After aging for 15 min, analysis by HPLC of the reaction mixture indicated 18% probucol monosuccinate, 1% probucol disuccinate, and 81% probucol.

Example 43

In a dry 10 mL round bottom fitted with nitrogen inlet, thermocouple and stir bar was charged probucol (1.0 g, 1.93 mmol) followed by 2 mL anhydrous THF. To the resulting solution was slowly added benzylmagnesium chloride (1.97 mL, 2.0 M in THF) at such a rate to maintain the internal reaction temperature between 40-50° C. Once addition was complete DMF (4 mL) was added and the reaction was aged at room temperature. Iodo-acetic acid ethyl ester (0.24 mL, 2.03 mmol) was added to the resulting solution in 1 portion. The reaction was heated to 60° C. and aged overnight. Analysis by HPLC of the reaction mixture indicated ca. 70% probucol and 30% probucol-acetic acid ethyl ester (a probucol monoether) of the following formula

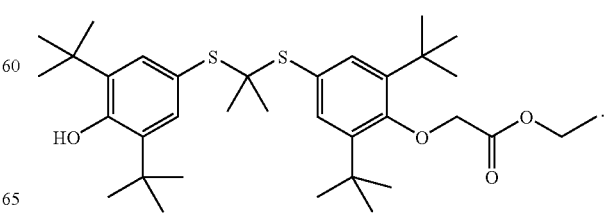

Example 44

In a dry 10 mL round bottom fitted with nitrogen inlet, thermocouple and stir bar was charged probucol (1.0 g, 1.93 mmol) followed by 2 mL anhydrous THF. To the resulting solution was slowly added benzylmagnesium chloride (1.97 mL, 2.0 M in THF) at such a rate to maintain the internal reaction temperature between 40-50° C. Once addition was complete DMF (4 mL) was added followed by sodium iodoacetate (0.44 g, 2.12 mmol) and the resulting solution was heated to 60° C. and aged overnight. Analysis by HPLC of the reaction mixture following an acid quench indicated ca. 98% probucol and 2% probucol-acetic acid (a probucol monoether) of Formula XVI

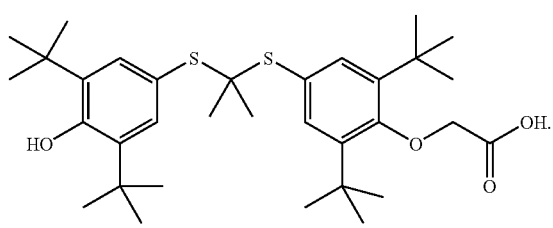

XVI

From the foregoing description, one skilled in the art can easily ascertain the essential characteristics of this invention, and without departing from the spirit and scope thereof, can make various changes and modifications of the invention to adapt it to various usages and conditions.

I claim:

1. A process of manufacturing a compound of Formula I or salts thereof

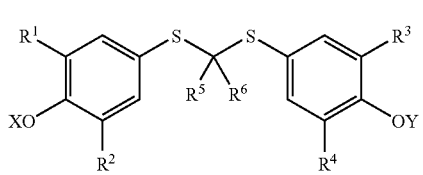

I wherein $R^1$, $R^2$, $R^3$, and $R^4$ are independently selected from the group consisting of hydrogen and alkyl, said alkyl optionally substituted by hydroxy, alkyl, alkenyl, acyl, nitro, amino, halo, carboxy and cyano;
$R^5$ and $R^6$ are the same or different and independently selected from the group consisting of alkyl, alkenyl, and aryl all of which can be optionally substituted by hydroxy, alkyl, alkenyl, acyl, nitro, amino, halo, carboxy and cyano;
$R^5$ and $R^6$ can come together to form a carbocyclic ring;
X is selected from the group consisting of hydrogen, an optionally substituted unsaturated acyl having from 1 to 18 carbon atoms, and an optionally substituted saturated acyl having from 1 to 18 carbon atoms, said optionally substituted unsaturated acyl and optionally substituted saturated acyl optionally containing a polar or charged functionality;
Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

comprising:
reacting a compound of Formula II

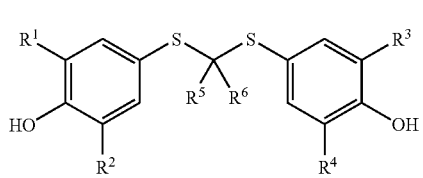

II wherein $R^1$, $R^2$, $R^3$, $R^4$, $R^5$ and $R^6$ are as previously defined, with an arylalkylmagnesium halide in the presence of a solvent, co-solvent or solubilizing reagent or mixtures thereof to form a magnesium salt; reacting said magnesium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, amino, halo, protected carboxy and cyano; separating and isolating said compound of Formula I.

2. The process of claim 1, wherein $R^1$, $R^2$, $R^3$, and $R^4$ are independently alkyl, said alkyl optionally substituted by hydroxy, alkyl, alkenyl, acyl, nitro, amino, halo, carboxy and cyano;
$R^5$ and $R^6$ are alkyl which can be optionally substituted by hydroxy, alkyl, alkenyl, acyl, nitro, amino, halo, carboxy and cyano;
X is H;
Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality.

3. The process of claim 2, wherein $R^1$, $R^2$, $R^3$, and $R^4$ are t-butyl;
$R^5$ and $R^6$ are methyl;
X is H;
Y is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality.

4. The process of claims 1, 2 or 3, wherein the arylalkylmagnesium halide is benzylmagnesium chloride.

5. The process of claim 1, wherein the solvent comprises THF, toluene or a mixture thereof.

6. The process of claim 5, wherein the solvent comprises THF.

7. The process of claim 1, wherein the magnesium salt is reacted with a saturated or unsaturated acyl halide.

8. The process of claim 1, wherein the magnesium salt is reacted with a saturated or unsaturated carboxylic acid anhydride.

9. The process of claim 8, wherein the saturated or unsaturated carboxylic acid anhydride is succinic anhydride.

10. The process of claim 1, wherein the magnesium salt is reacted with a saturated or unsaturated activated carboxylic acid ester.

11. A process of manufacturing a compound of Formula V or salts thereof

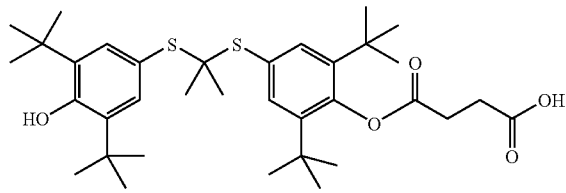

comprising:
reacting a compound of Formula IV

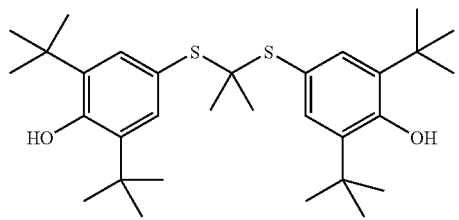

with an arylalkylmagnesium halide in the presence of a solvent, co-solvent or solubilizing reagent or mixtures thereof to form a magnesium salt; reacting said magnesium salt with a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, amino, halo, protected carboxy and cyano;
separating and isolating said compound of Formula V.

12. The process of claim 11, wherein the arylalkylmagnesium halide is benzylmagnesium chloride.

13. The process of claim 12, wherein the solvent comprises THF, toluene or a mixture thereof.

14. The process of claim 13, wherein the solvent comprises THF.

15. The process of claim 14, wherein the magnesium salt is reacted with a saturated or unsaturated acyl halide.

16. The process of claim 14, wherein the magnesium salt is reacted with succinic anhydride.

17. The process of claim 14, wherein the magnesium salt is reacted with a saturated or unsaturated activated carboxylic acid ester.

* * * * *